United States Patent
Fuchiwaki et al.

(10) Patent No.: US 9,997,715 B2
(45) Date of Patent: Jun. 12, 2018

(54) MATERIAL FOR ORGANIC ELECTROLUMINESCENT DEVICE AND ORGANIC ELECTROLUMINESCENT DEVICE USING THE SAME

(71) Applicant: SAMSUNG DISPLAY CO., LTD., Yongin-si, Gyeonggi-do (KR)

(72) Inventors: Junta Fuchiwaki, Yokohama (JP); Masatsugu Ueno, Yokohama (JP); Hiroaki Itoi, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 190 days.

(21) Appl. No.: 14/923,312

(22) Filed: Oct. 26, 2015

(65) Prior Publication Data

US 2016/0141509 A1    May 19, 2016

(30) Foreign Application Priority Data

Nov. 18, 2014    (JP) .................................. 2014-233980

(51) Int. Cl.
*H01L 51/50* (2006.01)
*H01L 51/00* (2006.01)
(Continued)

(52) U.S. Cl.
CPC ........ *H01L 51/0061* (2013.01); *C07D 307/91* (2013.01); *C09K 11/06* (2013.01);
(Continued)

(58) Field of Classification Search
None
See application file for complete search history.

(56) References Cited

U.S. PATENT DOCUMENTS 7,740,958 B2    6/2010 Saitoh et al.
7,927,719 B2    4/2011 Hwang et al.
(Continued)

FOREIGN PATENT DOCUMENTS

CN    102190627 A    9/2011
EP    2 042 481 A1    4/2009
(Continued)

OTHER PUBLICATIONS

European Patent Office Abstract Publication No. JP 2006-151844 A, dated Jun. 15, 2006, for JP 4677221 B2, 2 pages.
(Continued)

*Primary Examiner* — Gregory D Clark
(74) *Attorney, Agent, or Firm* — Lewis Roca Rothgerber Christie LLP

(57) ABSTRACT

A material for an organic electroluminescent device having high emission efficiency and an organic electroluminescent device utilizing the same. The material is represented by Formula 1.

Formula 1

(Continued)

In Formula 1, $X_1$ to $X_7$ are each independently hydrogen, deuterium, a halogen atom, an alkyl group having 1 to 15 carbon atoms, or a substituted or unsubstituted aryl group; $Ar_1$ and $Ar_2$ are each independently a substituted or unsubstituted aryl group having 6 to 12 carbon atoms for forming a ring; L is a substituted or unsubstituted arylene group; n is an integer from 1 to 3; at least one L is a phenylene group represented by Formula 2.

Formula 2

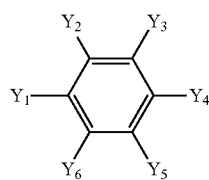

(2)

In Formula 2, $Y_1$ to $Y_6$ are each independently a direct linkage, hydrogen, deuterium, halogen, an alkyl group having 1 to 15 carbon atoms, an alkenyl group having 2 to 15 carbon atoms, or a substituted or unsubstituted aryl group.

12 Claims, 1 Drawing Sheet

(51) Int. Cl.
  *C07D 307/91* (2006.01)
  *C09K 11/06* (2006.01)
(52) U.S. Cl.
  CPC ........ *H01L 51/006* (2013.01); *H01L 51/0073* (2013.01); *H01L 51/0058* (2013.01); *H01L 2251/308* (2013.01)

(56) References Cited

U.S. PATENT DOCUMENTS

| | | |
|---|---|---|
| 8,057,918 B2 | 11/2011 | Marks et al. |
| 8,188,315 B2 | 5/2012 | Hwang et al. |
| 8,304,095 B2 | 11/2012 | Heil et al. |
| 8,710,493 B2 | 4/2014 | Nishimura et al. |
| 2004/0265630 A1 | 12/2004 | Suh et al. |
| 2005/0067951 A1 | 3/2005 | Richter et al. |
| 2007/0205715 A1 | 9/2007 | Saitoh et al. |
| 2008/0106188 A1 | 5/2008 | Hwang et al. |
| 2011/0297923 A1 | 12/2011 | Mizuki et al. |
| 2012/0112174 A1 | 5/2012 | Lee et al. |
| 2013/0153878 A1 | 6/2013 | Mizuki et al. |
| 2013/0293094 A1 | 11/2013 | Dyatkin et al. |
| 2013/0328027 A1 | 12/2013 | Sotoyama et al. |
| 2015/0270502 A1 | 9/2015 | Fuchiwaki et al. |

FOREIGN PATENT DOCUMENTS

| | | |
|---|---|---|
| EP | 2 348 017 A1 | 7/2011 |
| EP | 2 351 760 A1 | 8/2011 |
| EP | 2 421 064 A2 | 2/2012 |
| EP | 2 468 725 A1 | 6/2012 |
| EP | 2 484 665 A1 | 8/2012 |
| EP | 2 423 206 B1 | 1/2014 |
| JP | 05-323634 A | 12/1993 |
| JP | 8179526 A | 7/1996 |
| JP | 20000 86595 A | 3/2000 |
| JP | 3278252 B2 | 4/2002 |
| JP | 2005-516059 A | 6/2005 |
| JP | 2007-230951 A | 9/2007 |
| JP | 2008-021687 A | 1/2008 |
| JP | 2009-185024 A | 8/2009 |
| JP | 2009-194042 A | 8/2009 |
| JP | 2010-143841 A | 7/2010 |
| JP | 2010-195708 A | 9/2010 |
| JP | 4538752 B2 | 9/2010 |
| JP | 4677221 B2 | 4/2011 |
| JP | 2012-049518 A | 3/2012 |
| JP | 2012-186021 A | 9/2012 |
| JP | 5107237 B2 | 12/2012 |
| JP | 2013-063930 A | 4/2013 |
| JP | 2013-063931 A | 4/2013 |
| JP | 2013-75891 A | 4/2013 |
| JP | 2013-093432 A | 5/2013 |
| JP | 2013-107853 A | 6/2013 |
| JP | 2013-525346 A | 6/2013 |
| JP | 5242917 B2 | 7/2013 |
| JP | 5323634 B2 | 10/2013 |
| JP | 2013-234182 A | 11/2013 |
| JP | 5405630 B2 | 2/2014 |
| JP | 5443501 B2 | 3/2014 |
| JP | 5460894 B2 | 4/2014 |
| JP | 5617398 B2 | 11/2014 |
| JP | 2015-122381 A | 7/2015 |
| KR | 10-2009-0058063 A | 6/2009 |
| KR | 10-2009-0073925 A | 7/2009 |
| KR | 10-2010-0039393 | 4/2010 |
| KR | 10-2010-0079458 A | 7/2010 |
| KR | 10-2011-0056728 A | 5/2011 |
| KR | 10-2011-0068239 | 6/2011 |
| KR | 10-2011-0069077 A | 6/2011 |
| KR | 10-2012-0024624 A | 3/2012 |
| KR | 10-2012-0066149 A | 6/2012 |
| KR | 10-2011-0030303 * | 8/2013 ............ H01L 51/50 |
| KR | 10-1298483 B1 | 8/2013 |
| KR | 10-2014-0074228 | 6/2014 |
| WO | WO 2004/020387 A1 | 3/2004 |
| WO | WO 2006/073059 A1 | 7/2006 |
| WO | WO 2006/128800 A1 | 12/2006 |
| WO | WO 2007/070778 A2 | 6/2007 |
| WO | WO 2007/105906 A1 | 9/2007 |
| WO | WO 2007/148660 A1 | 12/2007 |
| WO | WO 2008/015963 A1 | 2/2008 |
| WO | WO 2008/132085 A1 | 11/2008 |
| WO | WO 2009/145016 A1 | 12/2009 |
| WO | WO 2010/044130 A1 | 4/2010 |
| WO | WO 2010/052932 A1 | 5/2010 |
| WO | WO 2010/061824 A1 | 6/2010 |
| WO | WO 2010/110553 A2 | 9/2010 |
| WO | WO 2010-114017 A1 | 10/2010 |
| WO | WO 2010/122810 A1 | 10/2010 |
| WO | WO 2011/021520 A1 | 2/2011 |
| WO | WO 2011/040607 A1 | 4/2011 |
| WO | WO 2011/059099 A1 | 5/2011 |
| WO | WO 2011/077691 A1 | 6/2011 |
| WO | WO 2011/102112 A1 | 8/2011 |
| WO | WO 2012/056674 A1 | 5/2012 |
| WO | WO 2012/070227 A1 | 5/2012 |
| WO | WO 2012/091471 A2 | 7/2012 |
| WO | WO 2013/036044 A2 | 3/2013 |
| WO | WO 2013/039184 A1 | 3/2013 |

OTHER PUBLICATIONS

European Patent Office Abstract Publication No. WO 2006-128800 A1, dated Dec. 7, 2006, for JP 5107237 B2, 1 page.
European Patent Office Abstract Publication No. KR 2012-0111670 A, dated Oct. 10, 2012, for KR 10-1298483 B1, 2 pages.
U.S. Office Action dated Dec. 1, 2016, issued in U.S. Appl. No. 14/731,180 (18 pages).
U.S. Office Action dated Nov. 15, 2017, issued in cross-reference U.S. Appl. No. 14/836,866 (10 pages).

* cited by examiner

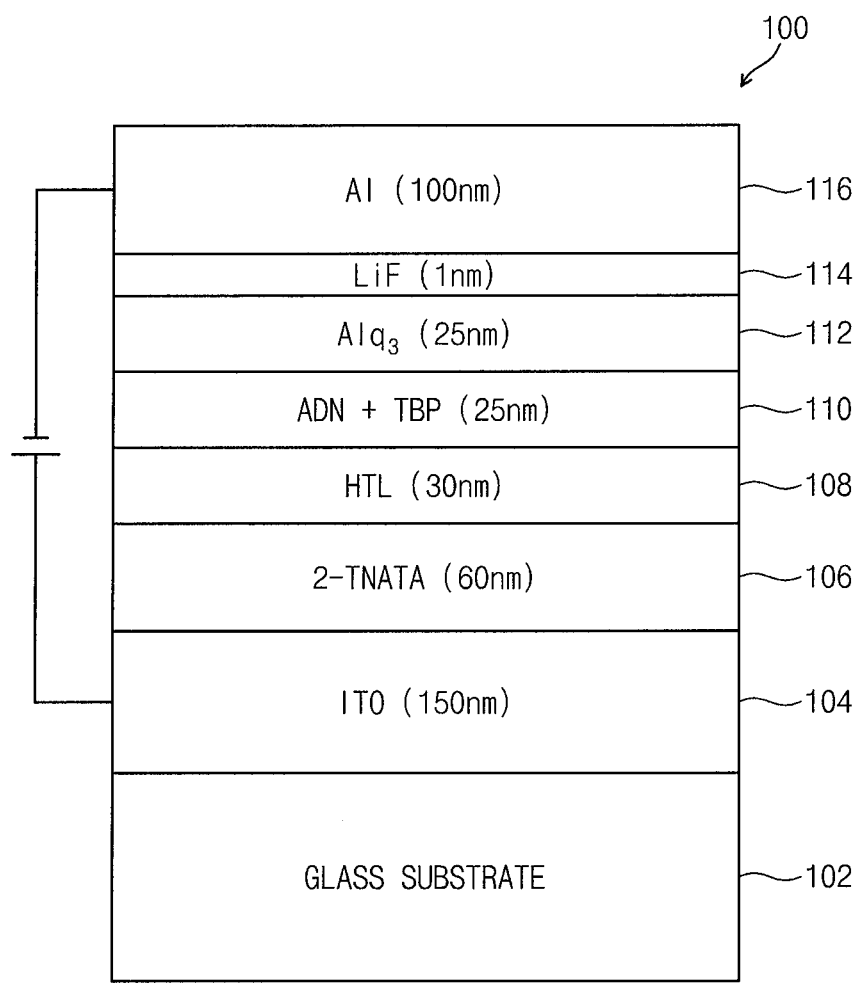

MATERIAL FOR ORGANIC ELECTROLUMINESCENT DEVICE AND ORGANIC ELECTROLUMINESCENT DEVICE USING THE SAME

CROSS-REFERENCE TO RELATED APPLICATION

This patent application claims priority to and the benefit of Japanese Patent Application No. 2014-233980, filed on Nov. 18, 2014, the entire content of which is incorporated herein by reference.

BACKGROUND

The present disclosure herein relates to a material for an organic electroluminescent device and an organic electroluminescent device utilizing the same. More particularly, the present disclosure herein relates to a material for an organic electroluminescence device having high emission efficiency when utilized in a layer between an emission layer and an anode, and an organic electroluminescence device utilizing the same.

In recent years, organic electroluminescent (EL) displays is one type of image displays that have been actively developed. Unlike a liquid crystal display and the like, the organic EL display is a so-called self-luminescent display which performs display by emitting light from a luminescent material (including an organic compound) in its emission layer through the recombination of holes and electrons injected from an anode and a cathode in the emission layer.

An example of an organic electroluminescence device (organic EL device) known in the art is an organic EL device which includes an anode, a hole transport layer disposed on the anode, an emission layer disposed on the hole transport layer, an electron transport layer disposed on the emission layer, and a cathode disposed on the electron transport layer. Holes injected from the anode are injected into the emission layer via the hole transport layer. Meanwhile, electrons are injected from the cathode, and then injected via the electron transport layer into the emission layer. The holes and the electrons injected into the emission layer are recombined to generate excitons within the emission layer. The organic EL device emits light by radiation deactivation of the excitons. Also, the organic EL device is not limited to the above-described configuration but may be changed in various suitable forms.

In the application of the organic EL device in a display apparatus, the high efficiency of the organic EL device is required. To realize the high efficiency of the organic EL device, the normalization and the stabilization of a hole transport layer have been examined. As a hole transport material utilized in a hole transport layer, a compound including carbazole or amine, and a compound obtained by combining thereof (e.g., a compound including both the carbazole group and the amine group) and having dibenzofuran and amine (e.g., a compound including both the dibenzofuran group and the amine group) may be utilized. For example, an amine compound including fluorene and dibenzofuran or an amine compound having a terphenyl group and dibenzofuran is generally utilized. However, since the compound including a terphenyl group or a fluorene ring structure is thermally decomposed by high temperature during the deposition process, it is undesirable in consideration of the manufacturing process. In addition, these compounds have high electron transport properties, and in the case that the compounds are applied in an electron blocking layer, the emission efficiency of an organic EL device may not be sufficiently improved.

As the hole transport material, a polyamine compound having dibenzofuran and (e.g., combined with) two or more amine parts (e.g., groups), an amine compound having carbazole and dibenzofuran, etc. may be utilized. In addition, a dibenzofuran derivative, an anthracene derivative having dibenzofuran and amine as substituents, a compound including an amino group making a direct linkage with dibenzofuran, dibenzofuran including a substituent having amine at position 2, a structure obtained by connecting 3-dibenzofuran group-phenyl group-amine, etc. may be utilized. Further, an amine derivative including a deuterated phenyl group, a monoamine material including diphenyl or triphenylated phenyl and dibenzofuran, etc. may be utilized. In addition, a monoamine material including a plurality of dibenzofuran combined at position 3 or a monoamine material including one dibenzofuran combined at a position other than 3 as the host of an emission layer of an organic EL device including a plurality of emission layers may be utilized. Meanwhile, a monoamine material including carbazole and dibenzofuran combined at position 3 may be utilized, and the combination of an amine material including dibenzofuran with a specific device structure may be utilized.

However, it may be difficult for an organic EL device utilizing these materials to have sufficient emission efficiency and emission life, and an organic EL device having higher emission efficiency is required as of now.

SUMMARY

Aspects according to embodiments of the present invention are directed towards a material for an organic EL device having high emission efficiency, and an organic EL device utilizing the same.

Particularly, the present disclosure provides a material for an organic EL device having high emission efficiency, utilized in a layer of stacking layers (stacked layers) disposed between an emission layer and an anode, and an organic EL device utilizing the same.

According to an embodiment of the present invention, a material for an organic EL device is represented by Formula 1.

Formula 1

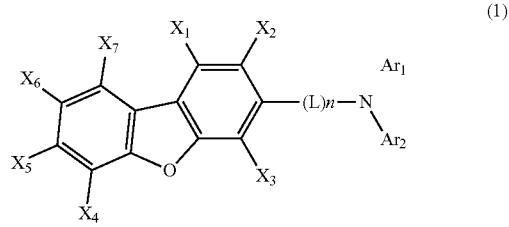

(1)

In Formula 1, $X_1$ to $X_7$ are each independently hydrogen, deuterium, a halogen atom, an alkyl group having 1 to 15 carbon atoms, or a substituted or unsubstituted aryl group; $Ar_1$ and $Ar_2$ are each independently a substituted or unsubstituted aryl group having 6 to 12 carbon atoms for forming a ring; L is a substituted or unsubstituted arylene group; n is an integer from 1 to 3; and at least one L is a phenylene group represented by Formula 2.

Formula 2

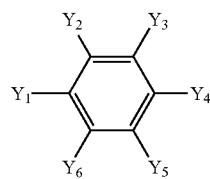
(2)

In Formula 2, $Y_1$ to $Y_6$ are each independently a direct linkage, hydrogen, deuterium, a halogen atom, an alkyl group having 1 to 15 carbon atoms, an alkenyl group having 2 to 15 carbon atoms, or a substituted or unsubstituted aryl group; two of $Y_1$ to $Y_6$ make a direct linkage with a respective adjacent group, and at least one of $Y_1$ to $Y_6$ of the at least one L is an aryl group.

The material for an organic EL device according to an embodiment of the inventive concept is an amine compound combined with a dibenzofuranyl group (with high hole tolerance and electron tolerance) at position 3 via a linker including at least one phenylene group substituted with at least one aryl group. In the material for an organic EL device according to an embodiment of the inventive concept, torsion angle between the benzene rings may increase due to the steric effect of the substituent of the linker, and emission efficiency may be higher due to molecules with high singlet excitation energy than an amine compound making a bond at position 2 as reported in the related arts.

In an embodiment, each of $Y_1$ and $Y_4$ among $Y_1$ to $Y_6$ of the phenylene group represented by Formula 2 may make a direct linkage with an adjacent group.

In the material for an organic EL device according to an embodiment of the inventive concept, each of $Y_1$ and $Y_4$ among $Y_1$ to $Y_6$ of the phenylene group makes a direct linkage with an adjacent group, and torsion angle between the benzene rings may increase due to the steric effect of the substituent of the phenylene group, and molecules having high singlet excitation energy may be obtained.

In an embodiment, at least one of $Y_1$ to $Y_6$ may be the aryl group having at least 10 carbon atoms for forming a ring.

In the material for an organic EL device according to an embodiment of the inventive concept, $Y_1$ to $Y_6$ of the phenylene group may be an aryl group having at least 10 carbon atoms for forming a ring or at least two aryl groups, and torsion angle between the benzene rings may increase due to the steric effect of the substituent of the phenylene group, and molecules having high singlet excitation energy may be obtained.

In an embodiment, $Ar_1$ and $Ar_2$ may be selected from the group consisting of a phenyl group, a biphenyl group and a naphthyl group.

In the material for an organic EL device according to an embodiment of the inventive concept, the number of atoms for forming a ring of $Ar_1$ and $Ar_2$ may be restricted, and thermal decomposition during forming a layer of an organic EL device by evaporation may be restrained.

In an embodiment, n may be 1.

Since the material for an organic EL device according to an embodiment of the inventive concept is an amine compound combined with a dibenzofuranyl group at position 3 via a linker including at least one phenylene group substituted with at least one aryl group, torsion angle between the benzene rings may increase due to the steric effect of the substituent of the phenylene group, and molecules having high singlet excitation energy may be obtained.

In an embodiment, the material for an organic EL device may be represented by one of Compounds 1 to 32.

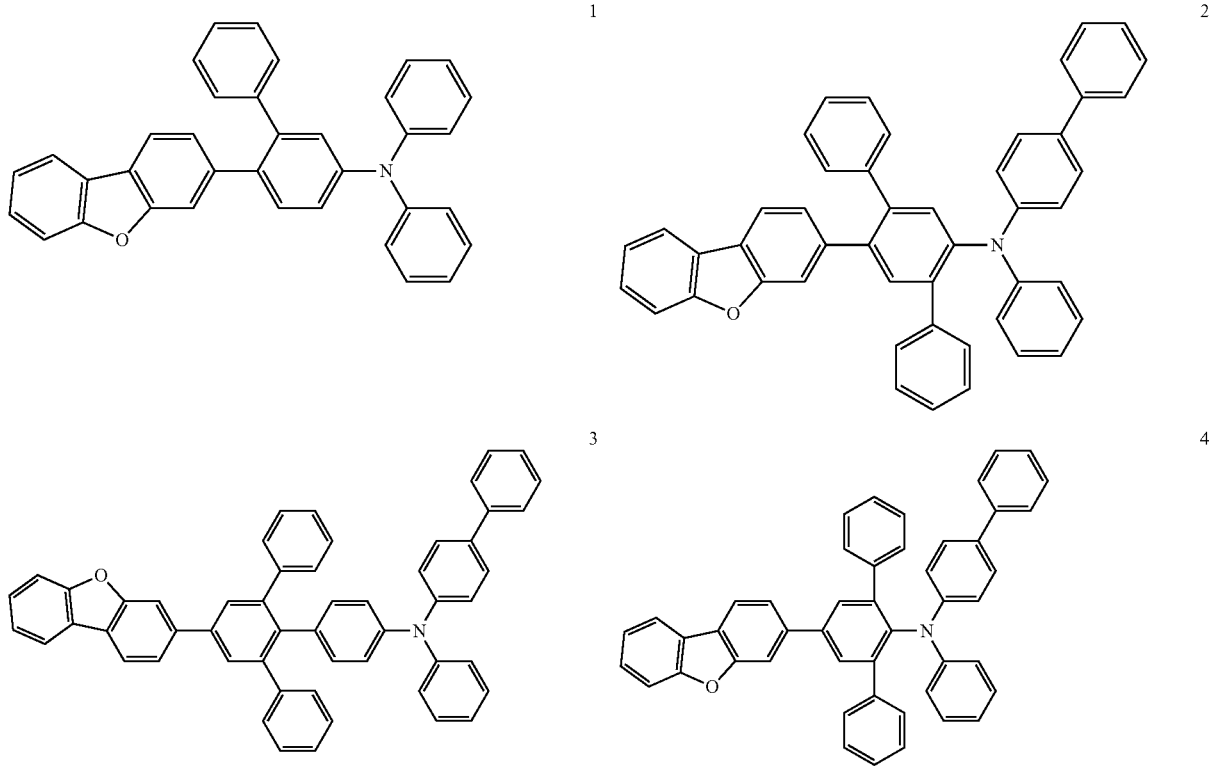

-continued
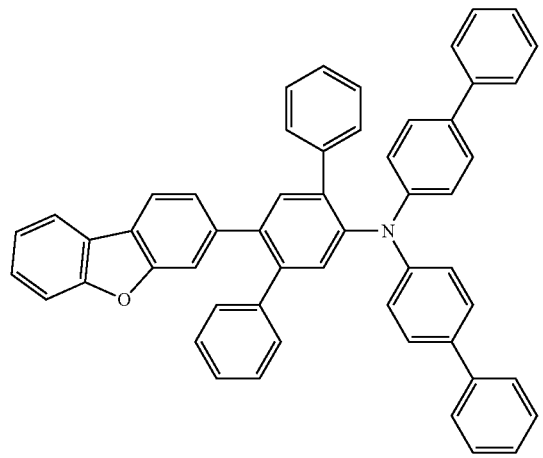
5
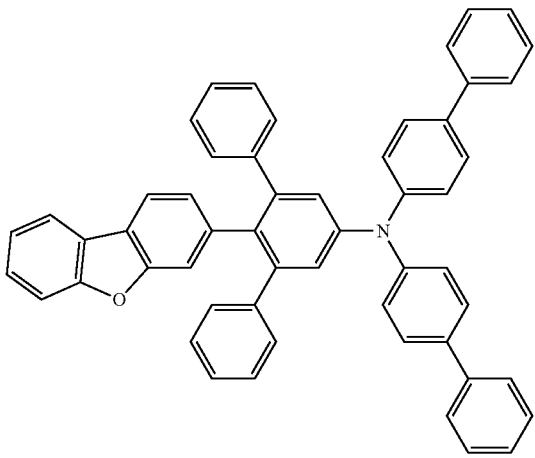
6
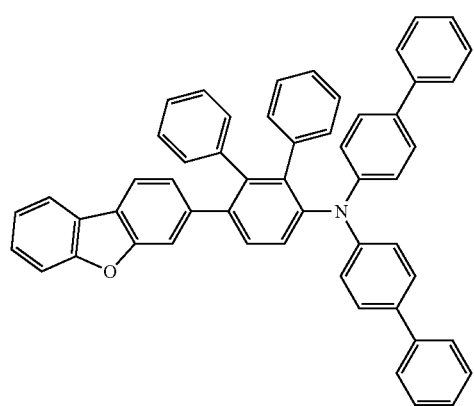
7
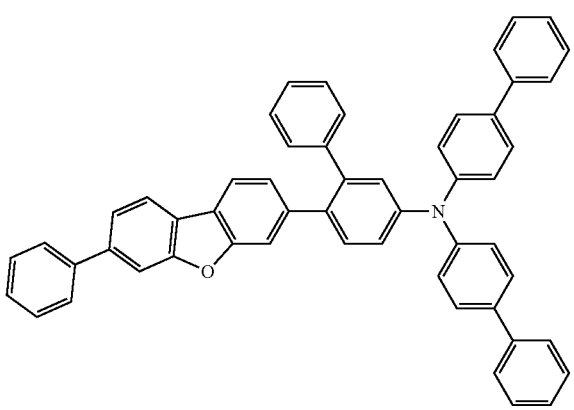
8
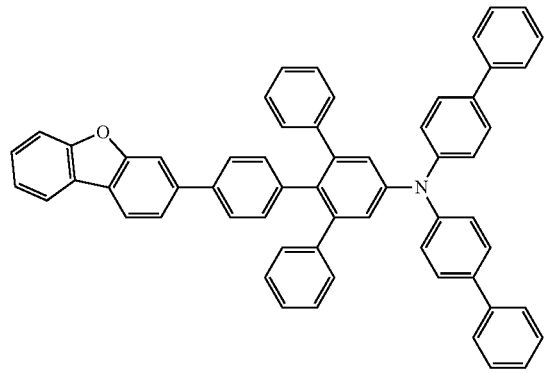
9
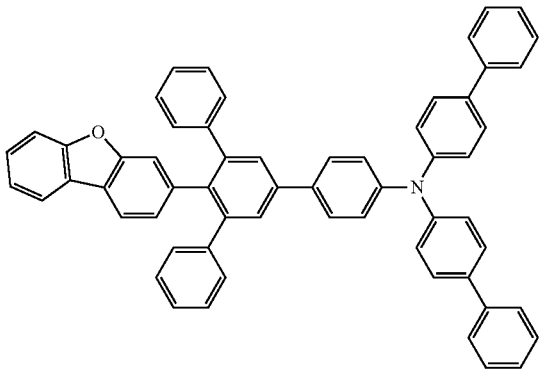
10

-continued
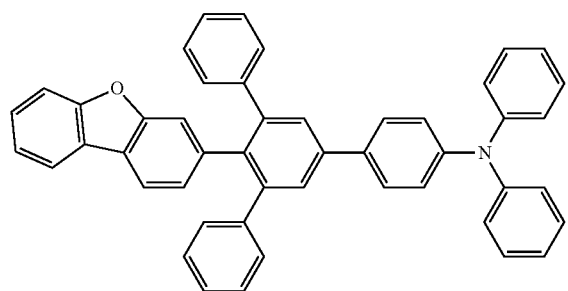
11
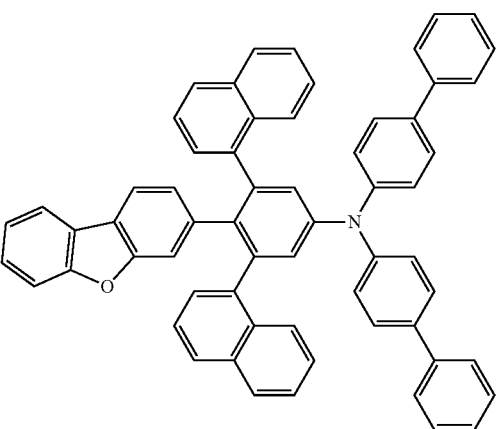
12
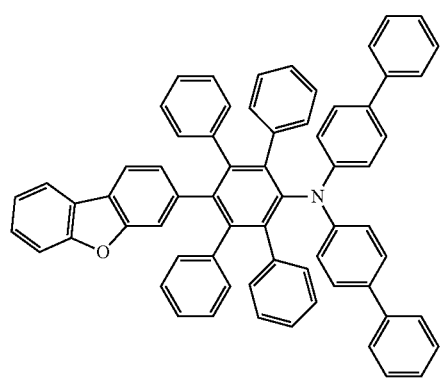
13
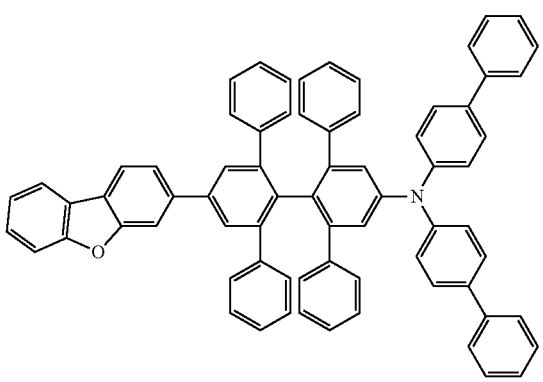
14
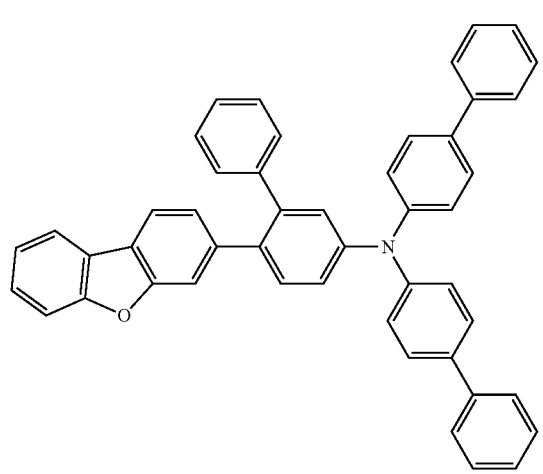
15
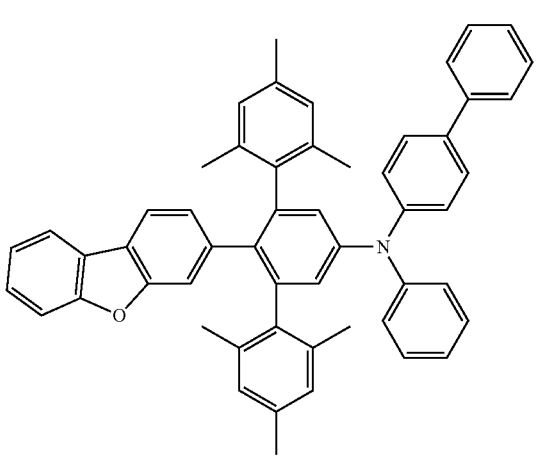
16

-continued
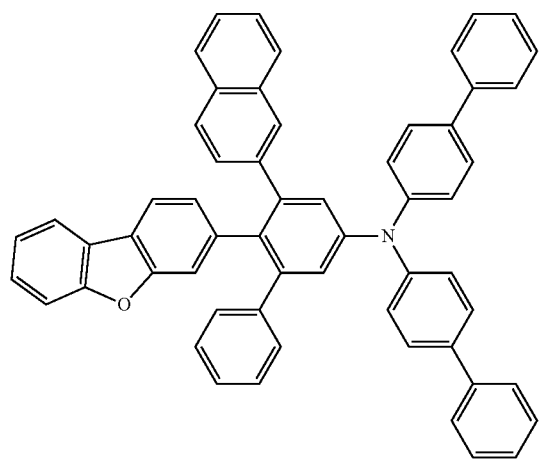
17
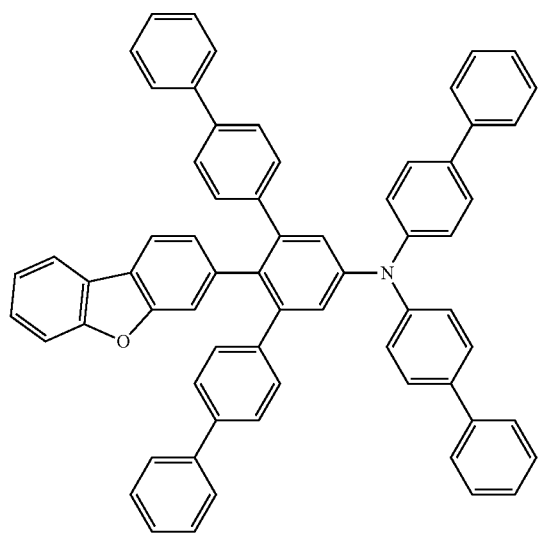
18
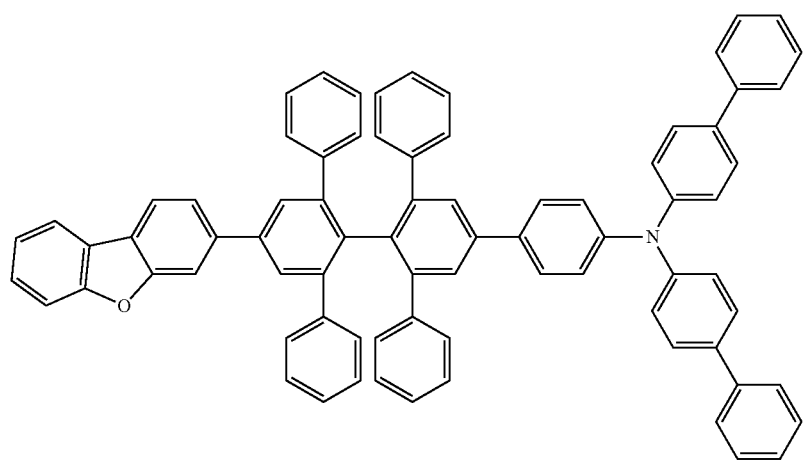
19
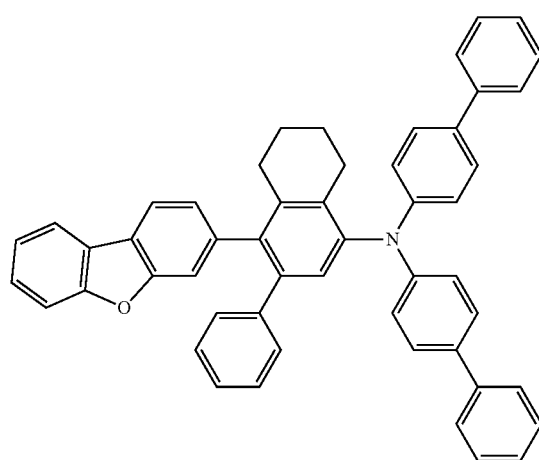
20
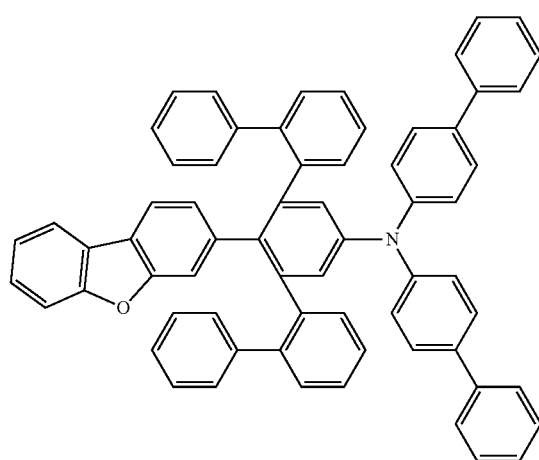
21

-continued
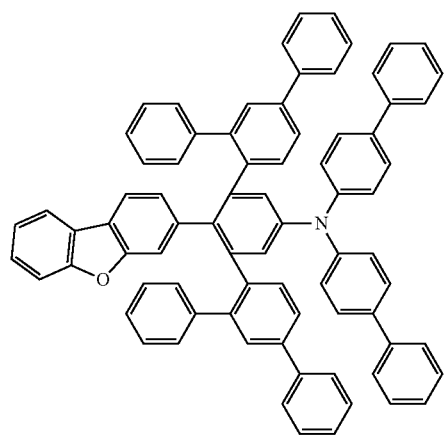
22
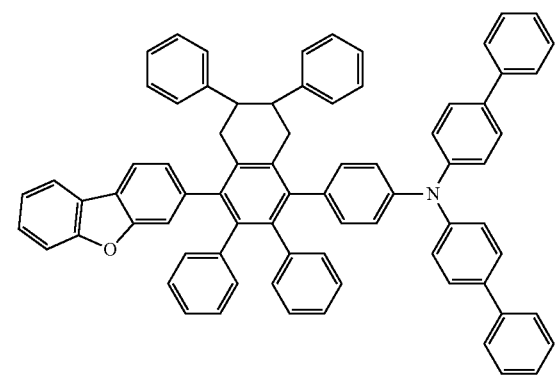
23
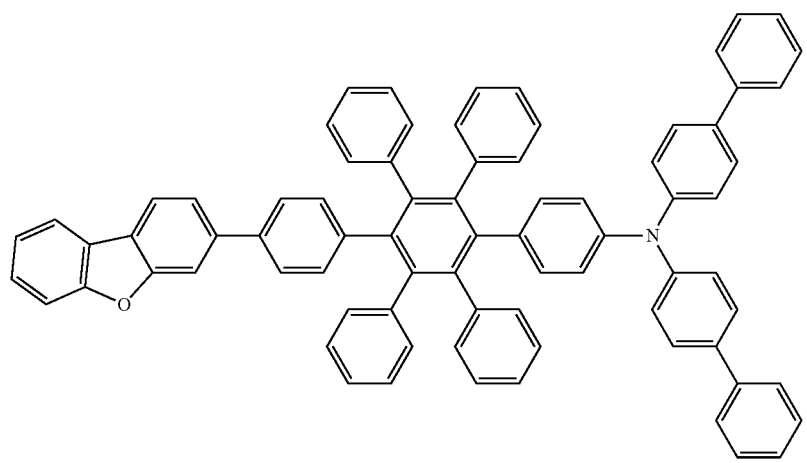
24
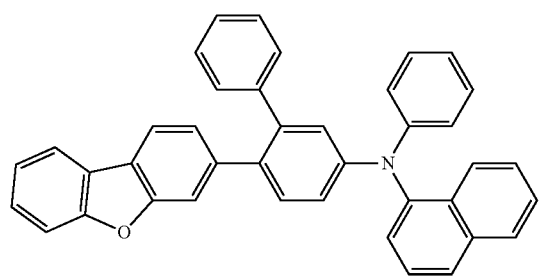
25
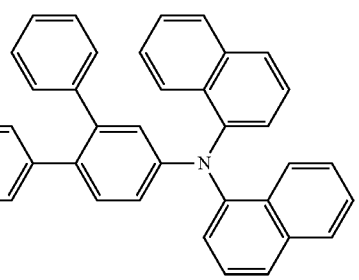
26
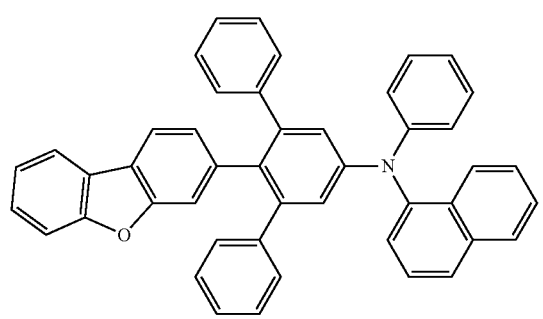
27
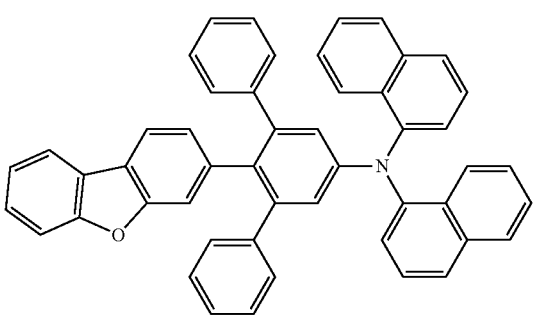
28

29

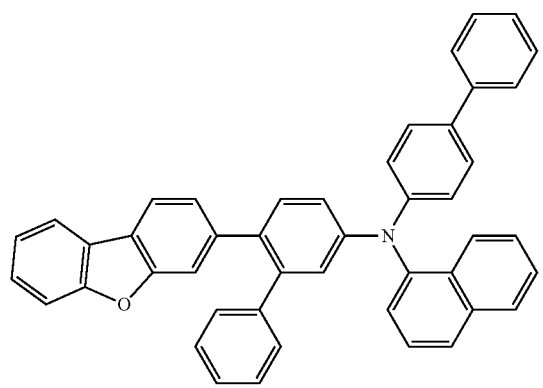

30

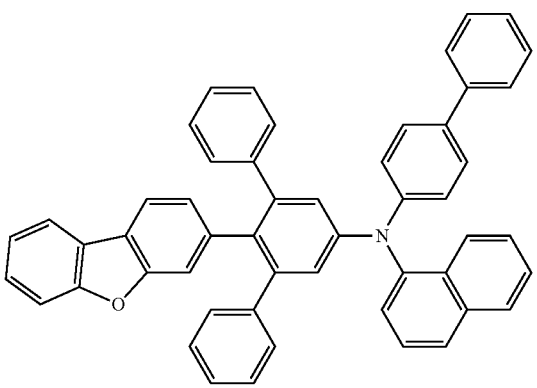

31

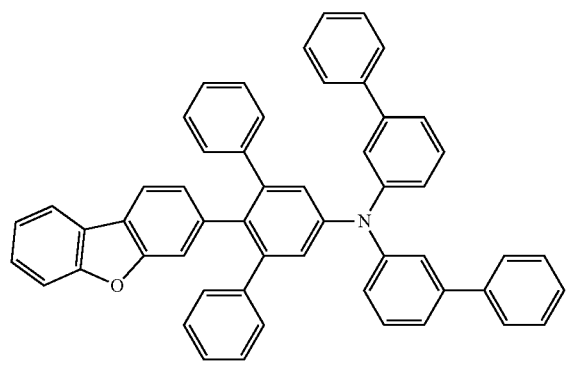

32

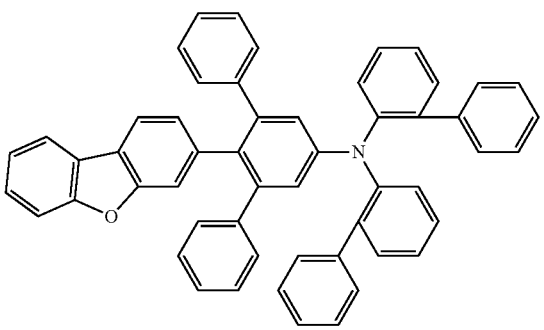

Since the material for an organic EL device according to an embodiment of the inventive concept is an amine compound combined with a dibenzofuranyl group (with high hole tolerance and electron tolerance) at position 3 via a linker including at least one phenylene group substituted with at least one aryl group, torsion angle between the benzene rings may increase due to the steric effect of the substituent of the linker, and emission efficiency may be higher than an amine compound making a bond at position 2 as reported in the related arts due to molecules with high singlet excitation energy.

In an embodiment of the inventive concept, an organic EL device includes one of the materials for an organic EL device in a layer of stacking layers between an emission layer and an anode.

Since the material for an organic EL device according to an embodiment of the inventive concept includes an amine compound combined with a dibenzofuranyl group (with high hole tolerance and electron tolerance) at position 3 via a linker including at least one phenylene group substituted with at least one aryl group in a layer of stacking layers disposed between an emission layer and an anode, torsion angle between the benzene rings may increase due to the steric effect of the substituent of the linker, and emission efficiency may be improved due to molecules with high singlet excitation energy.

BRIEF DESCRIPTION OF THE FIGURE

The accompanying drawing is included to provide a further understanding of the inventive concept, and is incorporated in and constitutes a part of this specification. The drawing illustrates example embodiments of the inventive concept and, together with the description, serves to explain principles of the inventive concept. The drawing is a schematic diagram illustrating an organic EL device 100 according to an embodiment of the inventive concept.

DETAILED DESCRIPTION

The inventors of the present disclosure thoroughly examined to solve the above-mentioned tasks and found that the increase of the emission efficiency of an organic EL device may be realized by combining an amine compound via a linker including at least one phenylene group substituted with at least one aryl group at position 3 of a dibenzofuranyl group instead of combining an amine compound via a linker at position 2 of a dibenzofuranyl group.

Hereinafter, a material for an organic EL device and an organic EL device utilizing the same according to the inventive concept will be described in more detail with reference to the accompanying drawing. The material for an organic EL device and the organic EL device including the same according to the inventive concept may, however, be embodied in different forms and should not be construed as limited to the embodiments set forth herein. In the description and drawings, elements having substantially the same function are designated by the same reference numerals, and repeated explanation thereof will not be provided again.

The material for an organic EL device according to an embodiment includes an amine compound combined via a linker including at least one phenylene group substituted with at least one aryl group with a dibenzofuranyl group at position 3 and is represented by the following Formula 1.

Formula 1

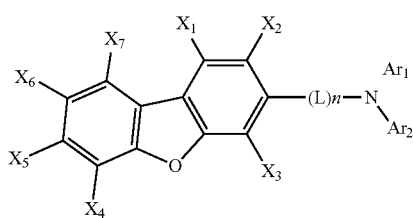

(1)

In the above Formula 1, $X_1$ to $X_7$ are each independently hydrogen, deuterium, a halogen atom, an alkyl group having 1 to 15 carbon atoms, or a substituted or unsubstituted aryl group. In one embodiment, the halogen atom may be a fluorine atom.

The alkyl group having 1 to 15 carbon atoms utilized as $X_1$ to $X_7$ may include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, a 1,2,3-trinitropropyl group, a cyclopropyl group, a cyclobutyl group, a cyclopentyl group, a cyclohexyl group, a 4-methylcyclohexyl group, a 1-adamantyl group, a 2-adamantyl group, a 1-norbornyl group, a 2-norbornyl group, etc., without being limited thereto.

As the substituted or unsubstituted aryl group utilized as $X_1$ to $X_7$, in one embodiment, an aryl group having 6 to 18 carbon atoms for forming a ring may be utilized and/or a phenyl group, a biphenylyl group, a 1-naphthyl group, a 2-naphthyl group, a fluorophenyl group, a difluorophenyl group, a trifluorophenyl group, a tetrafluorophenyl group, a pentafluorophenyl group, a toluyl group, a nitrophenyl group, a cyanophenyl group, a fluorobiphenylyl group, a nitrobiphenylyl group, a cyanobiphenylyl group, a cyanonaphthyl group, a nitronaphthyl group, a fluoronaphthyl group, a phenanthryl group, a terphenyl group, a fluoroterphenyl group, etc. may be utilized, without being limited thereto.

In Formula 1, $Ar_1$ and $Ar_2$ are each independently a substituted or unsubstituted aryl group having 6 to 12 carbon atoms for forming a ring. In one embodiment, substituents of $Ar_1$ and $Ar_2$ may include a fluoro group, a chloro group, an alkyl group having at most 12 carbon atoms, a fluoroalkyl group having at most 12 carbon atoms, a cycloalkyl group, an acetyl group, an arylether group, an arylsulfide group, etc., without being limited thereto.

As the substituted or unsubstituted aryl group having 6 to 12 carbon atoms for forming a ring utilized as $Ar_1$ and $Ar_2$, a phenyl group, a biphenylyl group, a 1-naphthyl group, a 2-naphthyl group, a fluorophenyl group, a difluorophenyl group, a trifluorophenyl group, a tetrafluorophenyl group, a pentafluorophenyl group, a toluyl group, a nitrophenyl group, a cyanophenyl group, a fluorobiphenylyl group, a nitrobiphenylyl group, a cyanobiphenylyl group, a cyanonaphthyl group, a nitronaphthyl group, a fluoronaphthyl group, etc., may be utilized without being limited thereto. In one embodiment, the phenyl group, the biphenylyl group, the naphthyl group and/or the fluorophenyl group may be utilized. For example, the phenyl group, the biphenylyl group and/or the naphthyl group may be utilized. By restricting the carbon number of $Ar_1$ and $Ar_2$ for forming a ring, thermal decomposition during forming a layer of an organic EL device by an evaporation method may be restrained (e.g., thermal decomposition of the compound represented by Formula 1 during the forming of a layer of an organic EL device by an evaporation method may be reduced or prevented).

In Formula 1, L is a substituted or unsubstituted arylene group, and n is an integer from 1 to 3. In the case that n is 2 or more, the two or more Ls may be the same or different. At least one of the Ls is a phenylene group represented by the following Formula 2.

Formula 2

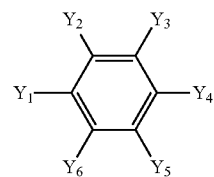

(2)

In Formula 2, $Y_1$ to $Y_6$ are each independently a direct linkage (i.e., a direct bond), hydrogen, deuterium, a halogen atom, an alkyl group having 1 to 15 carbon atoms, an alkenyl group having 2 to 15 carbon atoms, or a substituted or unsubstituted aryl group. Hereinafter, suitable functional groups utilized as $Y_1$ to $Y_6$ (other than a direct linkage or hydrogen) are also referred to as a substituent. Two of $Y_1$ to $Y_6$ make a direct linkage with an adjacent group (i.e., a respective adjacent group), and at least one of $Y_1$ to $Y_6$ of at least one of the phenylene group (e.g., at least one of $Y_1$ to $Y_6$ of the at least one of Ls represented by Formula 2) is an aryl group.

In an embodiment, each of $Y_1$ and $Y_4$ among $Y_1$ to $Y_6$ of the phenylene group may make a direct linkage with an adjacent group. By making a direct linkage of $Y_1$ and $Y_4$ among $Y_1$ to $Y_6$ of the phenylene group, and substituting at least one of $Y_2$, $Y_3$, $Y_5$ and $Y_6$ with an aryl group (e.g., substituting at least one hydrogen atom of the phenylene group represented by Formula 2 at $Y_2$, $Y_3$, $Y_5$ and $Y_6$ sites with an aryl group), torsion angle between the benzene rings in the phenylene group and an adjacent group may increase due to the steric effect of the substituent aryl group of the phenylene group and the adjacent group, and molecules with high singlet excitation energy may be obtained.

The alkyl group having 1 to 15 carbon atoms utilized as $Y_1$ to $Y_6$ may include a methyl group, an ethyl group, a propyl group, an isopropyl group, an n-butyl group, an n-s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, a 1,2,3-trinitropropyl group, a cyclopropyl group, a cyclobutyl group, a cyclopentyl group, a cyclohexyl group, a 4-methylcyclohexyl group, a 1-adamantyl group, a 2-adamantyl group, a 1-norbornyl group, a 2-norbornyl group, etc., without being limited thereto.

The alkenyl group having 2 to 15 carbon atoms utilized as $Y_1$ to $Y_6$ may include a vinyl group, a 1-propenyl group, a 2-propenyl group, a butenyl group, a pentenyl group, a hexenyl group, a heptenyl group, an octenyl group, a nonenyl group, a decenyl group, an undecenyl group, a styryl group, etc., without being limited thereto.

The substituted or unsubstituted aryl group utilized as $Y_1$ to $Y_6$ may include a phenyl group, a biphenylyl group, a naphthyl group, a phenanthryl group, a triphenylenyl group, a 2,3-diphenylphenyl group, a 2,4-diphenylphenyl group, a 2,5-diphenylphenyl group, a 3,5-diphenylphenyl group, a 3,4,5-triphenylphenyl group, a 2,4,6-triphenylphenyl group, a toluyl group, a 2,4-dimethylphenyl group, a 2,5-dimethylphenyl group, a 3,5-dimethylphenyl group, a 3,4,5-trimethylphenyl group, a 2,4,6-trimethylphenyl group, a 5,6,7,8-tetrahydronaphthyl group, a fluorenyl group, a 9,9-dimethylfluorenyl group, a 9,9-diphenylfluorenyl group, etc., without being limited thereto.

Here, the sum of the carbon number of at least one aryl group substituted for $Y_1$ to $Y_6$ of the phenylene group (e.g., the sum of the carbon number of the aryl group utilized for at least one of $Y_1$ to $Y_6$) may be at least 10, and in one embodiment, may be from 12 to 36. Since $Y_1$ to $Y_6$ can be substituted with 1 to 4 aryl groups (e.g., 1 to 4 of the $Y_1$ to $Y_6$ sites can be aryl groups), "the sum of the carbon number of at least one aryl group" described herein refers to the sum of the carbon number of the substituent aryl group for forming rings at one of the $Y_1$ to $Y_6$ sites. By substituting $Y_1$ to $Y_6$ of the phenylene group with a large aryl group having at least 10 carbon atoms for forming a ring or at least two aryl groups (e.g., a substituent with at least two rings fused together), torsion angle between the benzene rings may increase due to the steric effect of the substituent of the phenylene group, and molecules with high singlet excitation energy may be obtained.

In the case that adjacent two of $Y_1$ to $Y_6$ do not include one of a direct linkage, hydrogen or a halogen atom, the substituents thereof may combine with each other to form a ring.

The material for an organic EL device according to an embodiment of the inventive concept is an amine compound combined via a linker including at least one phenylene group substituted with at least one aryl group with a dibenzofuranyl group (having high hole tolerance and electron tolerance) at position 3. The material for an organic EL device according to an embodiment of the inventive concept has increased torsion angle between benzene rings due to the steric effect of the substituent of the linker and molecules with high singlet excitation energy, and is a material for an organic EL device having higher emission efficiency than an amine compound making a bond at position 2 reported in the related arts.

The material for an organic EL device according to an embodiment of the inventive concept may be represented by one of the following Compounds 1 to 6. However, the inventive concept is not limited thereto.

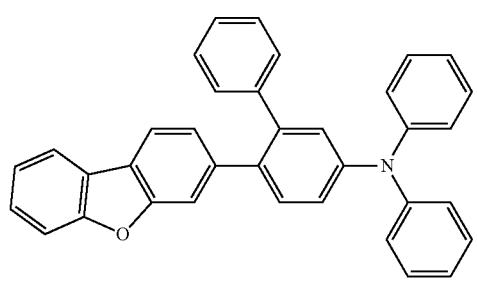

1

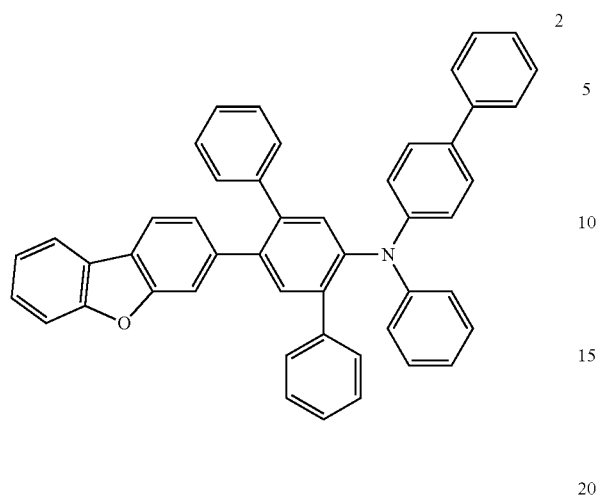
2
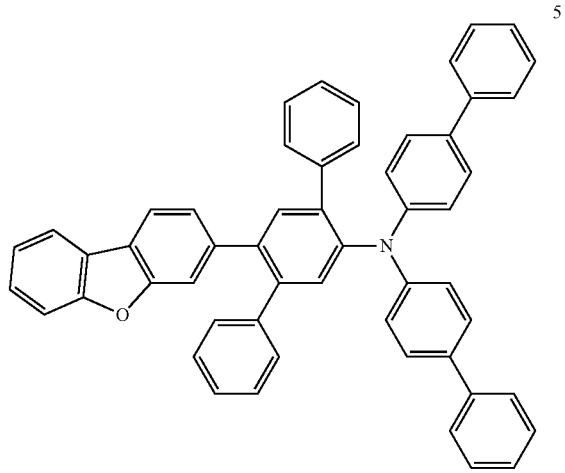
5
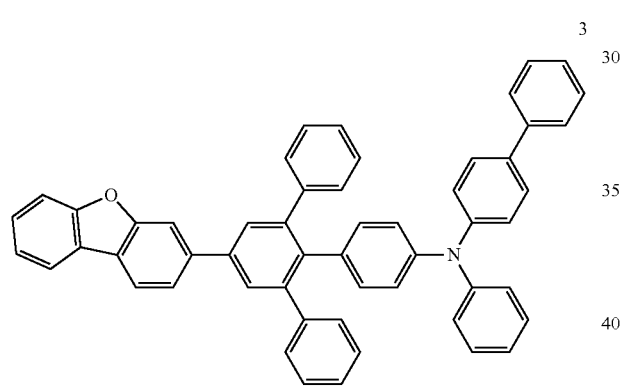
3
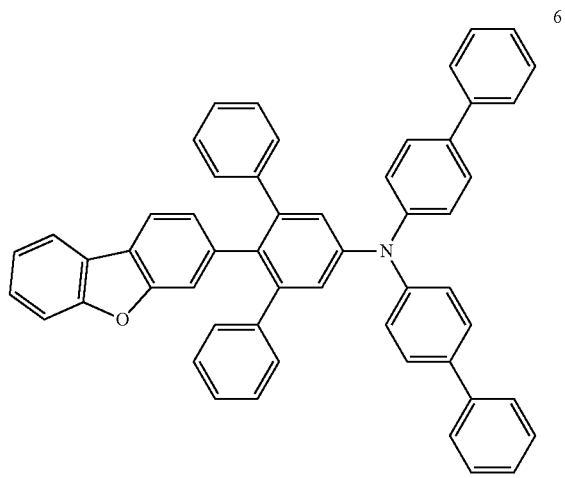
6
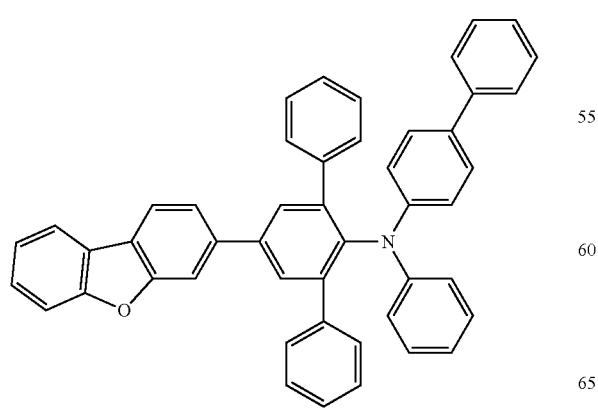
4
The material for an organic EL device according to an embodiment of the inventive concept may be represented by one of the following Compounds 7 to 12.
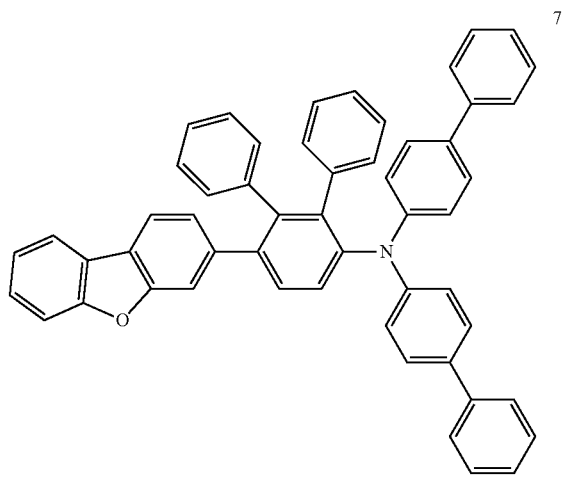
7

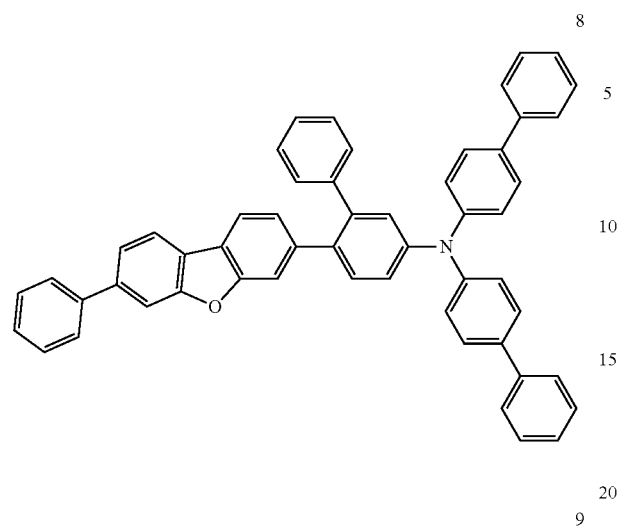
8
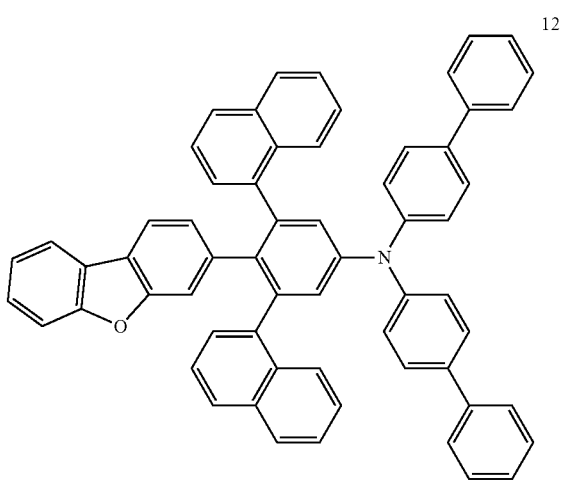
12
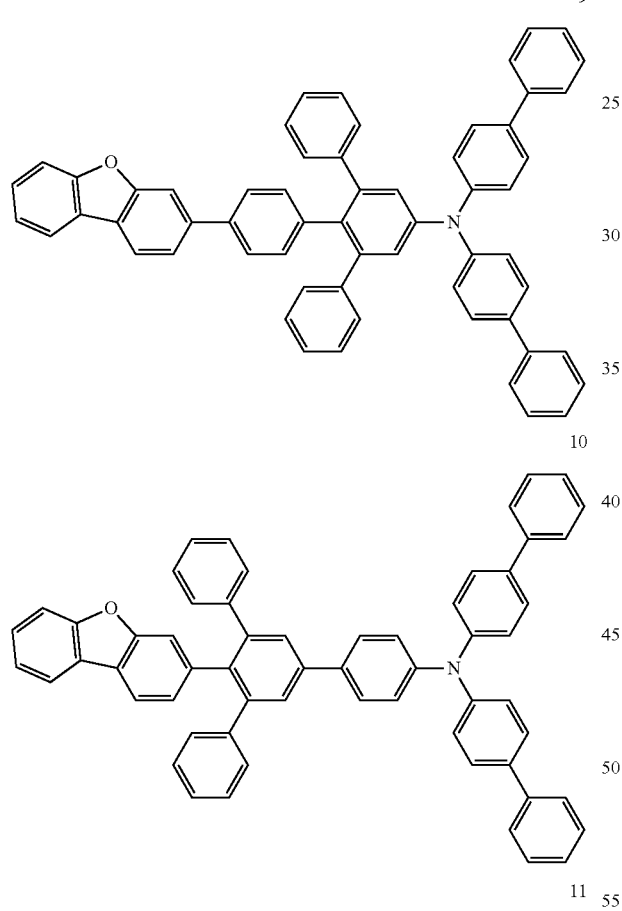
9
10
11
The material for an organic EL device according to an embodiment of the inventive concept may be represented by one of the following Compounds 13 to 18.
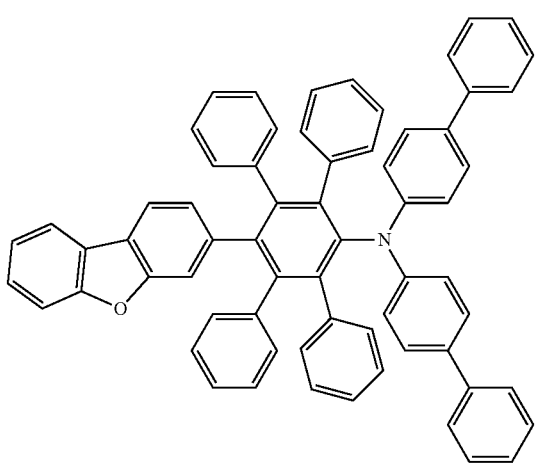
13
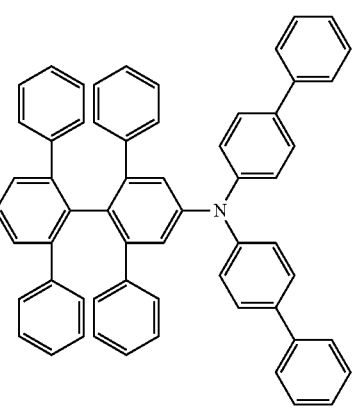
14

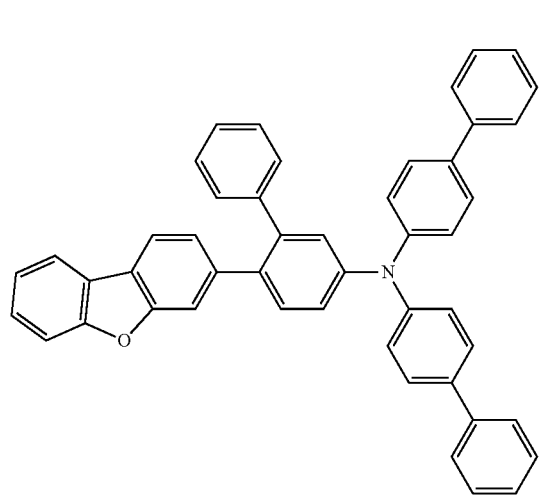
15
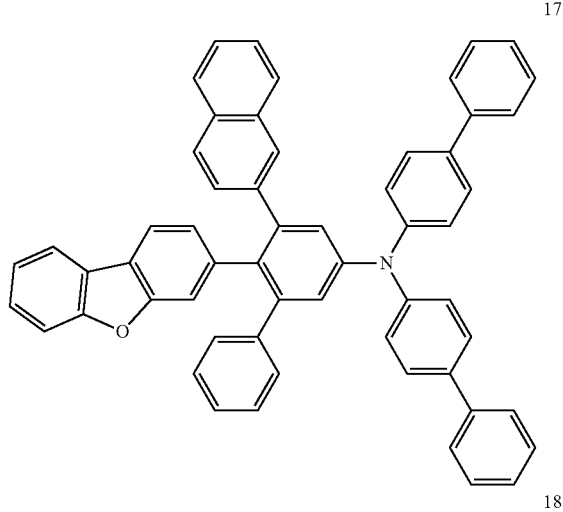
17
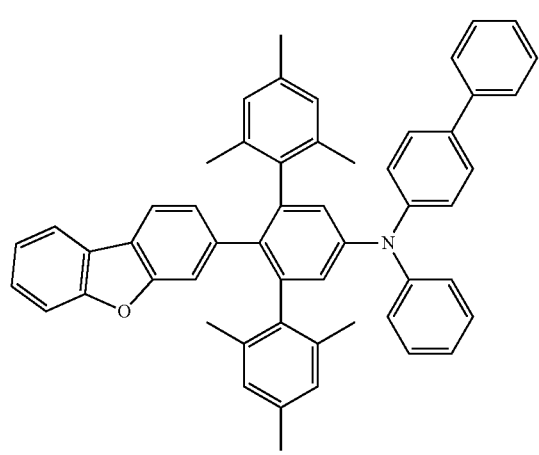
16
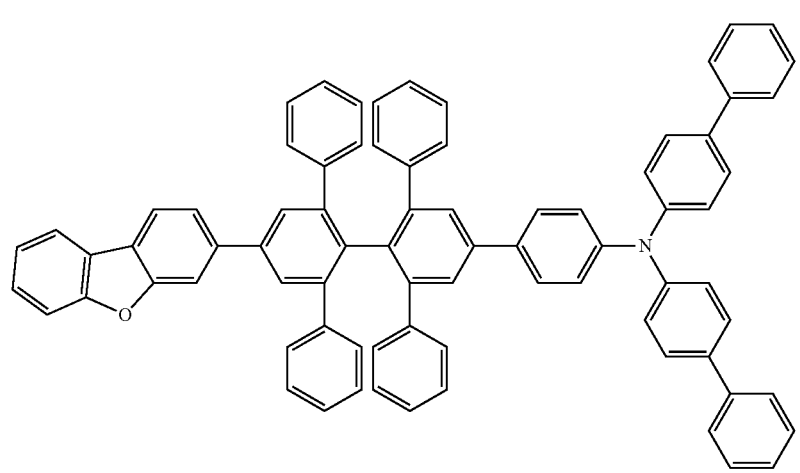
18
The material for an organic EL device according to an embodiment of the inventive concept may be represented by one of the following Compounds 19 to 24.
19

-continued
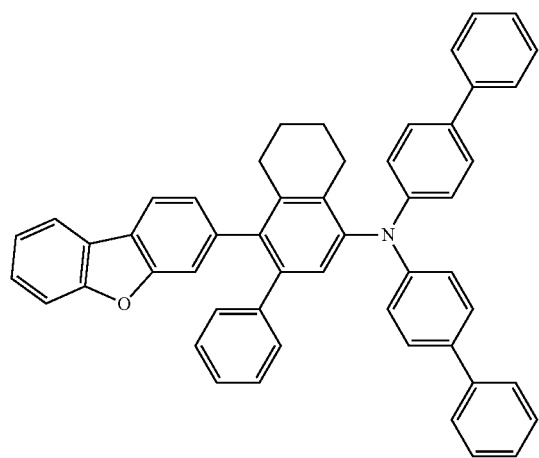
20
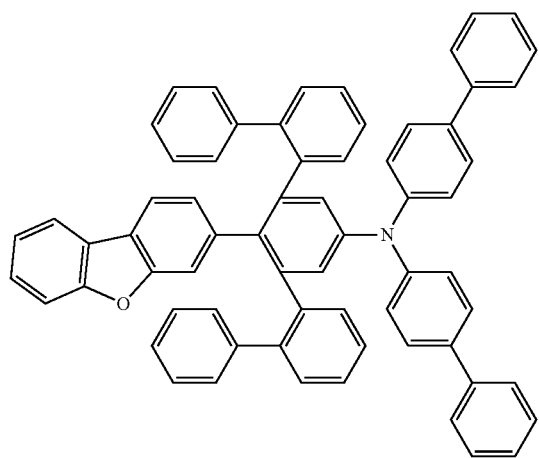
21
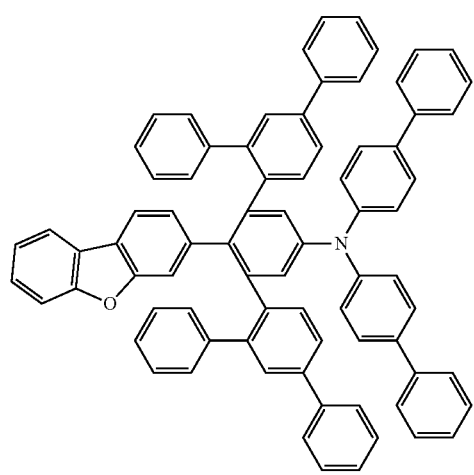
22
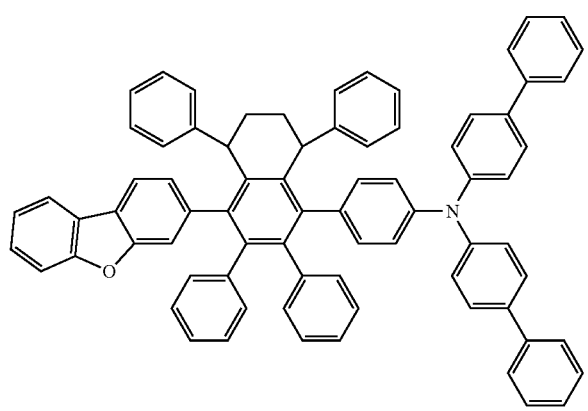
23
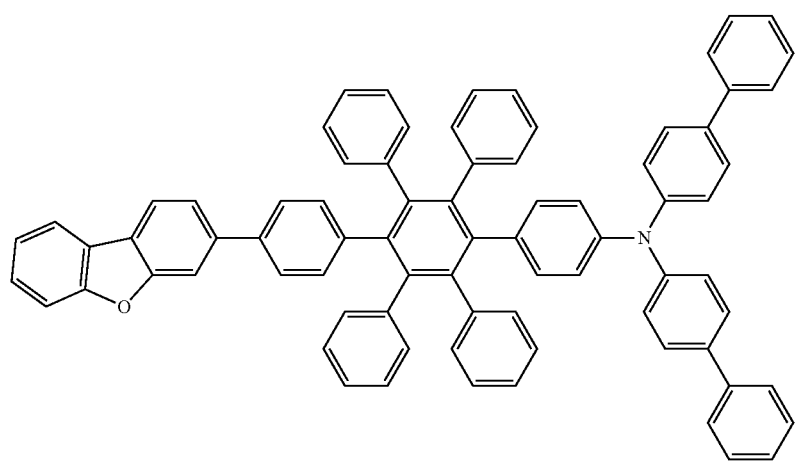
24

The material for an organic EL device according to an embodiment of the inventive concept may be represented by one of the following Compounds 25 to 32.
25
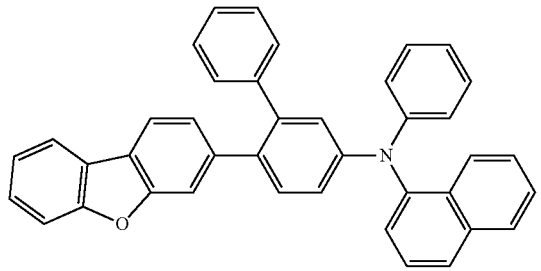
26
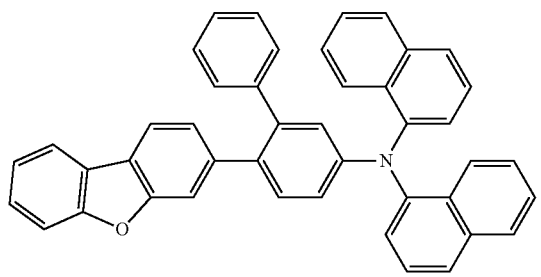
27
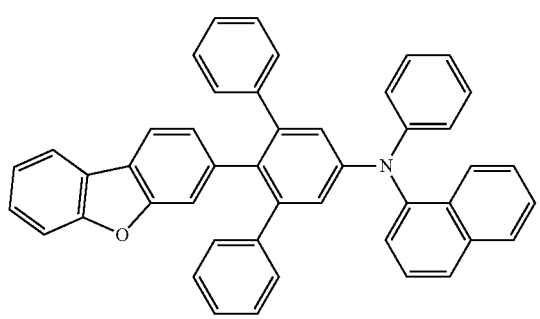
28
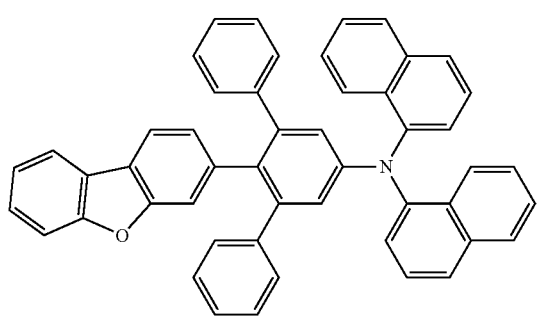
29
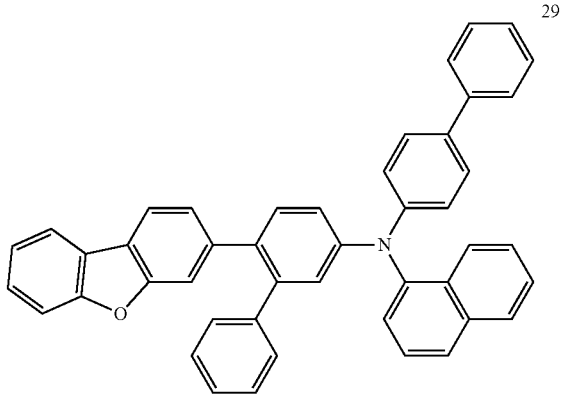
30
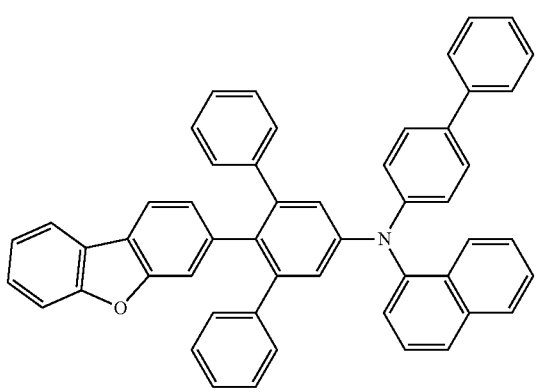
31
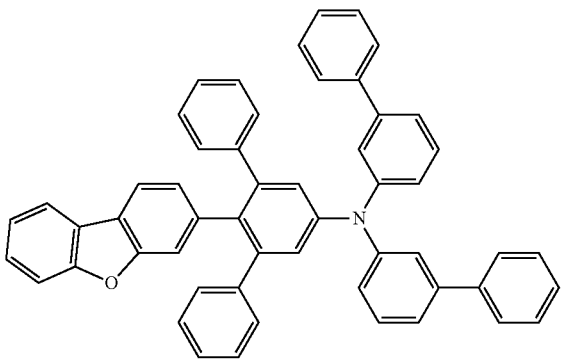

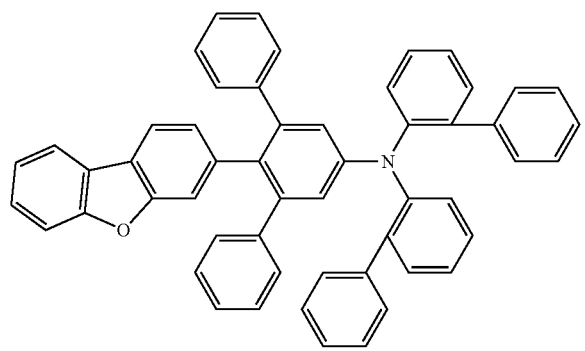

32

The material for an organic EL device according to an embodiment of the inventive concept may be utilized in a layer of stacking layers (e.g., utilized in one layer of a plurality of layers stacked over one another) disposed between an emission layer and an anode of an organic device. Thus, energy gap may increase, and high emission efficiency of an organic EL device may be realized.

(Organic EL Device)

An organic EL device utilizing the material for an organic EL device according to the inventive concept will be explained. The drawing is a schematic diagram illustrating an organic EL device 100 according to an embodiment. The organic EL device 100 may include, for example, a substrate 102, an anode 104, a hole injection layer 106, a hole transport layer 108, an emission layer 110, an electron transport layer 112, an electron injection layer 114 and a cathode 116. In an embodiment, the material for an organic EL device according to an embodiment of the inventive concept may be utilized in a layer of stacking layers (e.g., utilized in one of the layers stacked over one another and) disposed between the emission layer and the anode.

For example, an embodiment utilizing the material for an organic EL device according to the inventive concept in the hole transport layer 108 will be explained. The substrate 102 may be a transparent glass substrate, a semiconductor substrate formed utilizing silicon, etc., or a flexible substrate of a resin, etc. The anode 104 may be disposed on the substrate 102 and may be formed utilizing indium tin oxide (ITO), indium zinc oxide (IZO), etc.

The hole injection layer 106 may be disposed on the anode 104 and may include a compound represented by one of the following Formulae HI1 to HI3.

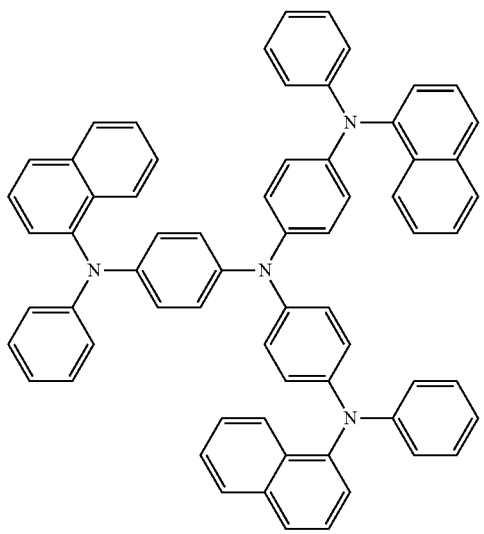

HI1

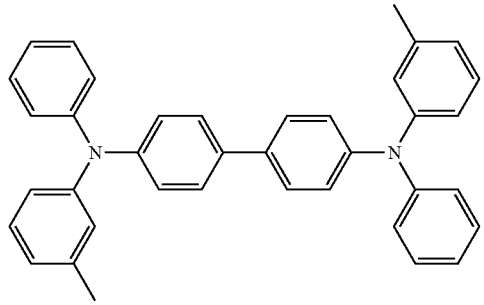

HI2

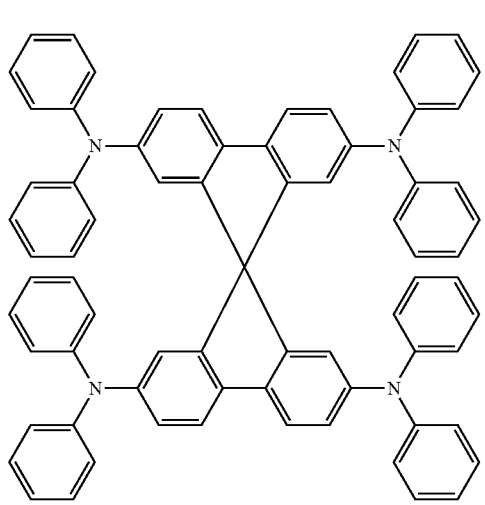

HI3

The hole transport layer 108 may be disposed on the hole injection layer 106 and may be formed utilizing the material for an organic EL device according to embodiments of the present invention.

The emission layer 110 may be disposed on the hole transport layer 108 and may be formed utilizing a host material represented by one of the following Formulae HO1 to HO4 doped with a luminescent material.

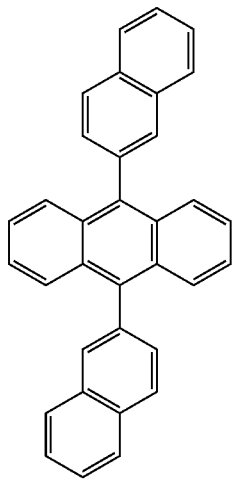

HO1

HO2
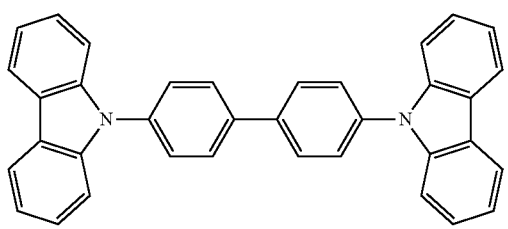
HO4
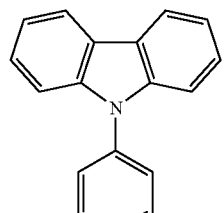
HO3
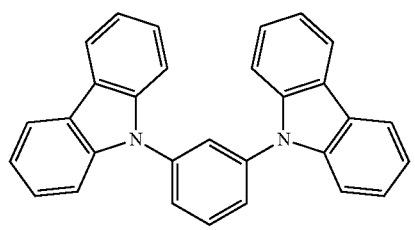
As the luminescent material doped in the emission layer 110, for example, a compound represented by one of the following Formulae DP1 to DP5 may be utilized. In addition, the luminescent material may be doped in the host material in a ratio within a range from about 0.1% to about 50% (e.g., based on a total weight of the host material and the luminescent material).
DP1
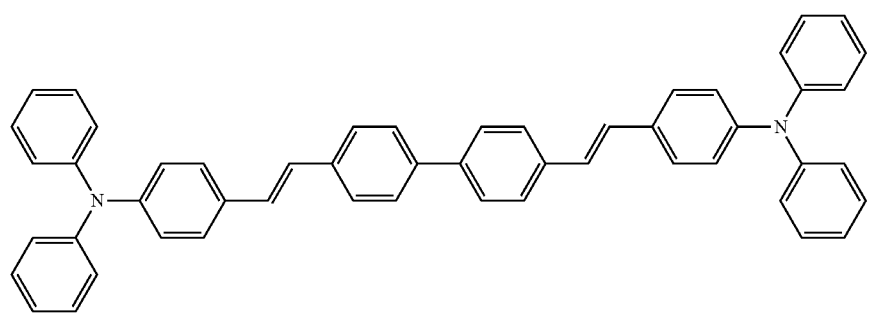
DP2
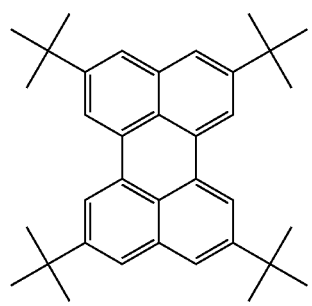
DP3
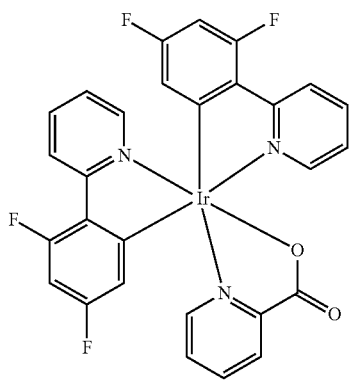

DP4

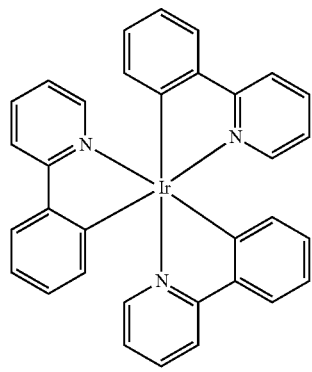

DP5

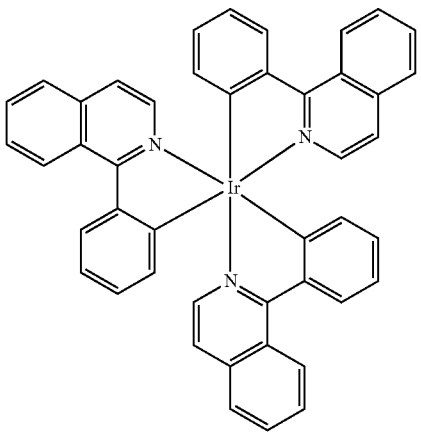

The electron transport layer 112 may be disposed on the emission layer 110 and may include, for example, a compound represented by one of the following Formulae ET1 to ET4.

ET1

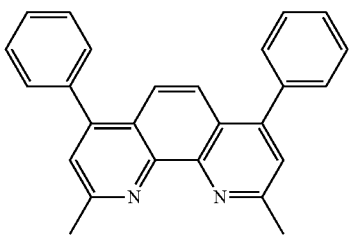

ET2

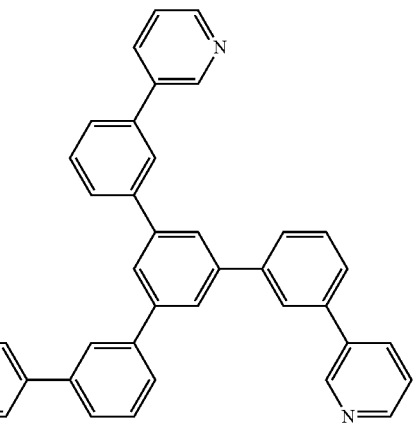

ET3

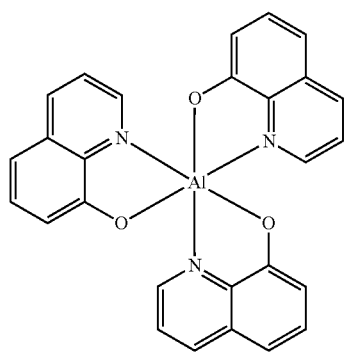

ET4

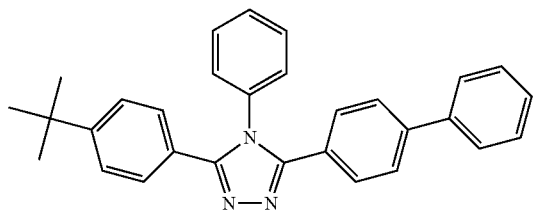

The electron injection layer 114 may be disposed on the electron transport layer 112 and may be formed utilizing, for example, a material including lithium fluoride (LiF), lithium-8-quinolinato, etc. The cathode 116 may be disposed on the electron injection layer 114 and may be formed utilizing a metal such as Al, Ag, Ca, etc. or a transparent material such as ITO, IZO, etc. The thin layers may be formed by selecting an appropriate layer forming method depending on a material such as a vacuum evaporation method, a sputtering method, various suitable coating methods, etc.

In an organic EL device 100 according to an embodiment of the inventive concept, a hole transport layer realizing high emission efficiency may be formed utilizing a material for an organic EL device according to an embodiment of the inventive concept. In addition, the material for an organic EL device according to an embodiment of the inventive concept may be applied in an organic EL display of an active matrix display utilizing a thin film transistor (TFT).

In the organic EL device 100 according to an embodiment of the inventive concept, the high emission efficiency may be realized by utilizing the material for an organic EL device in a layer of stacking layers disposed between an emission layer and an anode.

EXAMPLES

Preparation Method

The material for an organic EL device according to an embodiment of the inventive concept may be synthesized, for example, as follows.

(Synthesis of Compound 15)

Under an argon (Ar) atmosphere, 3.0 g of 6-bromo-[1,1'-biphenyl]-3-amine, 31.4 g of 4-idodobiphenyl, 0.88 g of tris(dibenzylideneacetone)dipalladium(O), 3.49 g of sodium t-butoxide, 70 ml of dry toluene and 1.27 ml of a 2M toluene solution of tri(t-butyl)phosphine were added to a 300 ml, three-necked flask, followed by stirring at room temperature for 12 hours to obtain a reaction mixture. Water was added to the reaction mixture, and an organic layer extracted with dichloromethane was distilled and dried to obtain a solid. The solid thus obtained was separated by flash column chromatography to obtain 3.0 g of an intermediate as a white solid (Yield 50%).

Under an argon atmosphere, 1.10 g of dibenzofuran-3-boronic acid, 2.87 g of the intermediate, 40 ml of toluene, 1.43 g of potassium carbonate, 0.6 g of tetrakis(triphenylphosphine)palladium(O), 3 ml of ethanol and 7 ml of water were added one by one to a 200 ml, three-necked flask, followed by heating and refluxing at 90° C. for 8 hours to obtain a reaction mixture. Water was added to the reaction mixture, and an organic layer extracted with dichloromethane was distilled and dried to obtain a solid. The solid thus obtained was separated by flash column chromatography to obtain 2.0 g of Compound 15 as a white solid (Yield 60%).

(Identification of Compound 15)

The molecular weight of Compound 15 measured by FAB-MS was 639.8.

Organic EL devices according to Examples 1 to 6 were manufactured utilizing Example Compounds 15, 11, 17, 6, 30 and 31 as hole transport materials by the above-described method. For comparison, organic EL devices according to Comparative Examples 1 and 2 were manufactured utilizing the following Comparative Compounds 1 and 2 as hole transport materials.

Compounds of Examples 1 to 6 (i.e., Example Compounds 15, 11, 17, 6, 30 and 31)

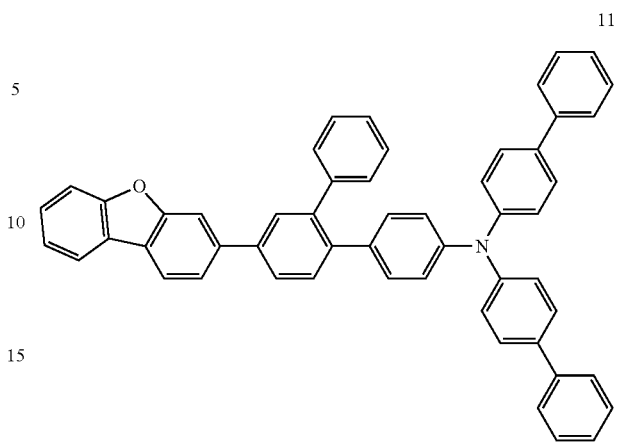

11

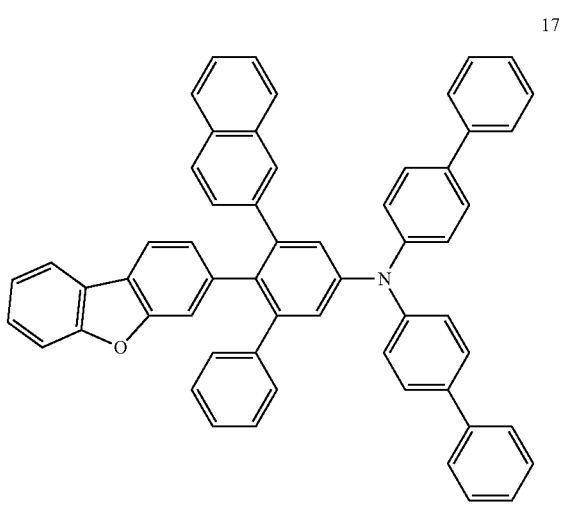

17

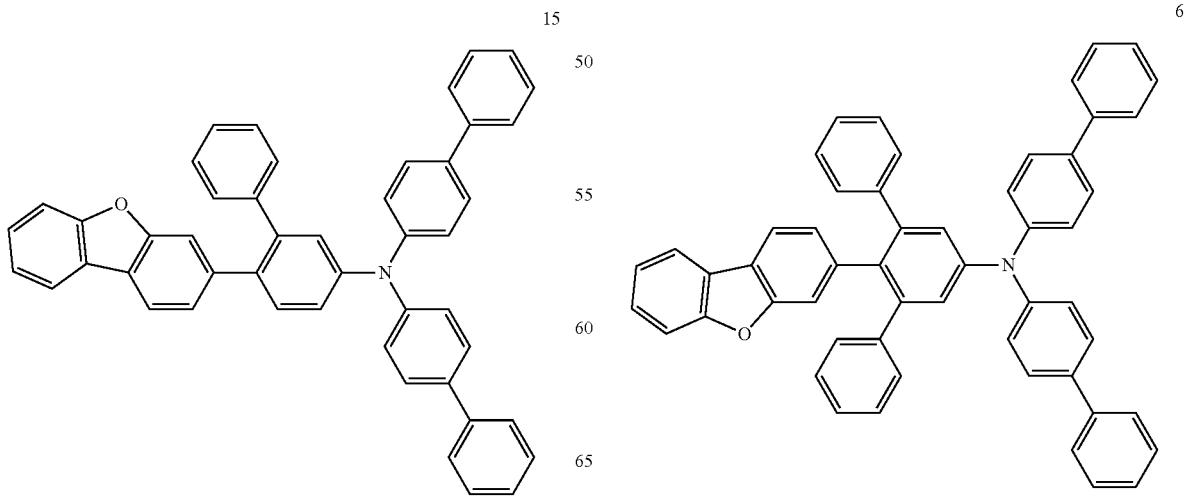

15

6

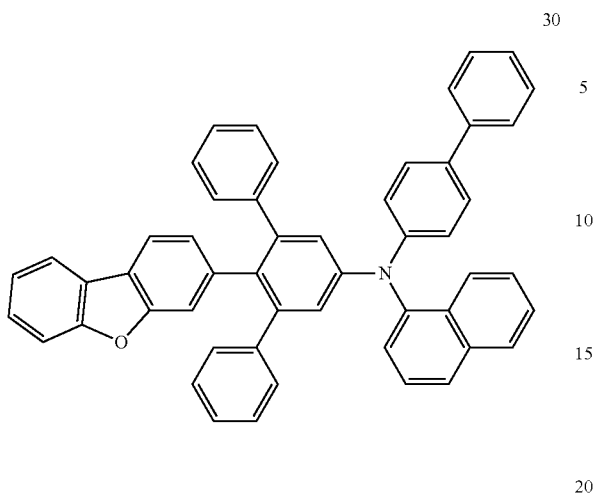

Comparative Compounds 1 and 2

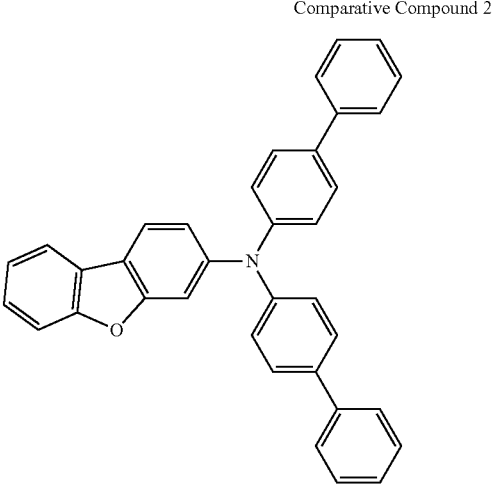

In this embodiment, the substrate 102 was formed utilizing a transparent glass substrate, the anode 104 was formed utilizing ITO to a thickness of about 150 nm, the hole injection layer 106 was formed utilizing 2-TNATA (HI1) to a thickness of about 60 nm, the hole transport layer (HTL) 108 was formed utilizing the compounds of the examples and the comparative examples to a thickness of about 30 nm, the emission layer 110 was formed utilizing ADN (HO1) doped with 3% TBP (DP2) to a thickness of about 25 nm, the electron transport layer 112 was formed utilizing $Alq_3$ (ET3) to a thickness of about 25 nm, the electron injection layer 114 was formed utilizing LiF to a thickness of about 1 nm, and the cathode 116 was formed utilizing Al to a thickness of about 100 nm.

With respect to the organic EL devices thus manufactured, voltages and emission efficiency were evaluated. The evaluation was conducted at the current density of 10 $mA/cm^2$. The evaluation results are shown in Table 1.

TABLE 1

| Device manufacturing Example | Hole transport material | Current density ($mA/cm^2$) | Voltage (V) | Emission efficiency (cd/A) |
| --- | --- | --- | --- | --- |
| Example 1 | Example Compound 15 | 10 | 7.5 | 8.9 |
| Example 2 | Example Compound 11 | 10 | 8.1 | 8.2 |
| Example 3 | Example Compound 17 | 10 | 8.3 | 8.2 |
| Example 4 | Example Compound 6 | 10 | 8.3 | 9.0 |
| Example 5 | Example Compound 30 | 10 | 8.6 | 9.0 |
| Example 6 | Example Compound 31 | 10 | 8.8 | 9.1 |
| Comparative Example 1 | Comparative Compound 1 | 10 | 7.5 | 5.2 |
| Comparative Example 2 | Comparative Compound 2 | 10 | 8.1 | 6.3 |

From the results in Table 1, it was observed that the emission efficiency of the organic EL devices was increased for Examples 1 to 6 when compared to that for the comparative examples. A material having a dibenzofuran skeleton including a substituent at position 3 had very high hole tolerance and electron tolerance, and the increase of the emission efficiency of an organic EL device was realized. In the case that the material for an organic EL device according to an embodiment of the inventive concept was applied in a hole transport layer, the emission efficiency was markedly (e.g., significantly) improved by blocking the introduction of electrons from an emission layer when compared to an organic EL device utilizing a commonly utilized comparative compound.

The results may be marked when the nitrogen atom of amine combines with a dibenzofuran group via a linker, particularly via a linker having a substituent such as a phenyl group. The high emission efficiency of an organic EL device is possibly obtained due to the increase of a torsion angle between the benzene rings due to the steric effect of the substituent of the linker, thereby producing molecules with high singlet excitation energy. However, the mechanism for achieving high emission efficiency of an organic EL device is not limited thereto.

According to the inventive concept, a material for an organic EL device having high emission efficiency and an organic EL device utilizing the same may be provided. Particularly, according to the inventive concept, a material for an organic EL device having high emission efficiency, and an organic EL device utilizing the same may be provided when the material is utilized in a layer of stacking layers disposed between an emission layer and an anode.

The above-disclosed subject matter is to be considered illustrative and not restrictive, and the appended claims are intended to cover all such modifications, enhancements, and other embodiments, which fall within the true spirit and scope of the inventive concept. Thus, to the maximum extent allowed by law, the scope of the inventive concept is to be determined by the broadest permissible interpretation of the following claims and their equivalents, and shall not be restricted or limited by the foregoing detailed description.

What is claimed is:

1. A material for an organic electroluminescent (EL) device represented by Formula 1:

Formula 1

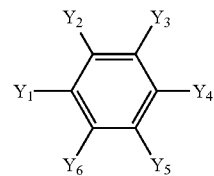

(1)

wherein in Formula 1,
$X_1$ to $X_7$ are each independently hydrogen, deuterium, a halogen atom, an alkyl group having 1 to 15 carbon atoms, or a substituted or unsubstituted aryl group;
$Ar_1$ and $Ar_2$ are each independently a substituted or unsubstituted aryl group having 6 to 12 carbon atoms for forming a ring;
L is a substituted or unsubstituted arylene group;
n is an integer from 1 to 3; and
at least one L is a phenylene group represented by Formula 2:

Formula 2

(2)

$$\begin{array}{c} Y_2 \quad Y_3 \\ Y_1 \diagup \diagdown Y_4 \\ Y_6 \quad Y_5 \end{array}$$

wherein in Formula 2,
$Y_1$ to $Y_6$ are each independently a direct linkage, hydrogen, deuterium, a halogen atom, an alkyl group having 1 to 15 carbon atoms, an alkenyl group having 2 to 15 carbon atoms, or a substituted or unsubstituted aryl group or may combine with an adjacent group to form a ring;
two of $Y_1$ to $Y_6$ make a direct linkage with a respective adjacent group; and
at least one of $Y_1$ to $Y_6$ of the at least one L is an aryl group.

2. The material for an organic EL device of claim 1, wherein each of $Y_1$ and $Y_4$ among $Y_1$ to $Y_6$ of the phenylene group represented by Formula 2 makes a direct linkage with an adjacent group.

3. The material for an organic EL device of claim 1, wherein at least one of $Y_1$ to $Y_6$ is the aryl group having at least 10 carbon atoms for forming a ring.

4. The material for an organic EL device of claim 1, wherein $Ar_1$ and $Ar_2$ are each independently selected from the group consisting of a phenyl group, a biphenyl group and a naphthyl group.

5. The material for an organic EL device of claim 1, wherein n is 1.

6. The material for an organic EL device of claim 1, wherein the material is represented by one of Compounds 1 to 32:

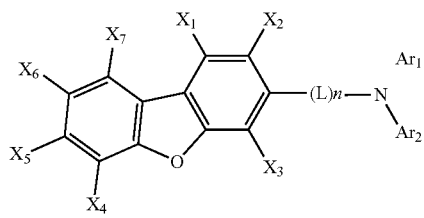

1

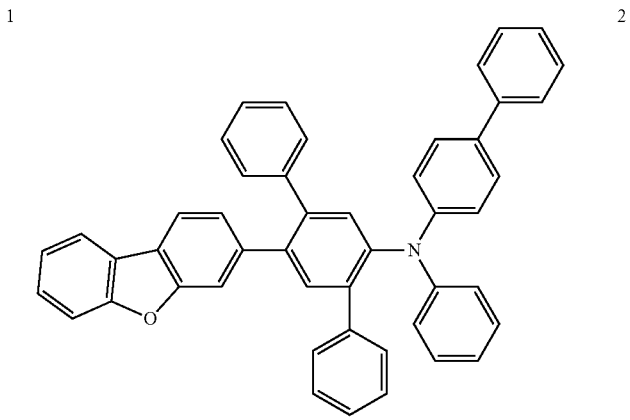

2

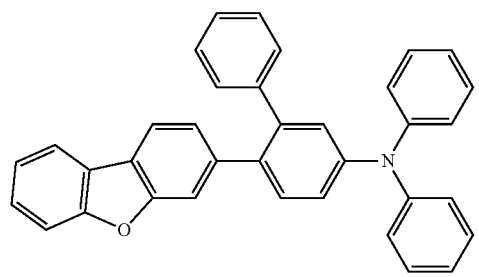

-continued
3
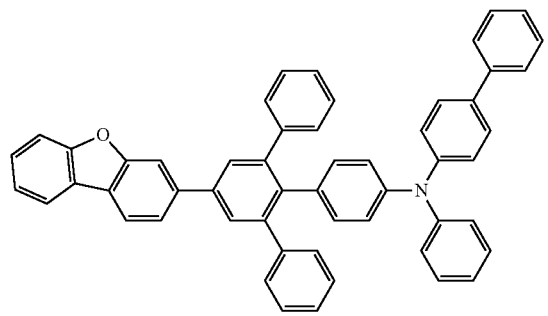
4
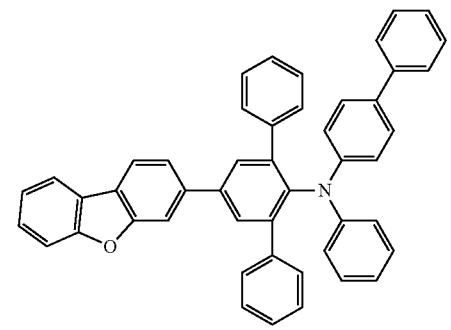
5
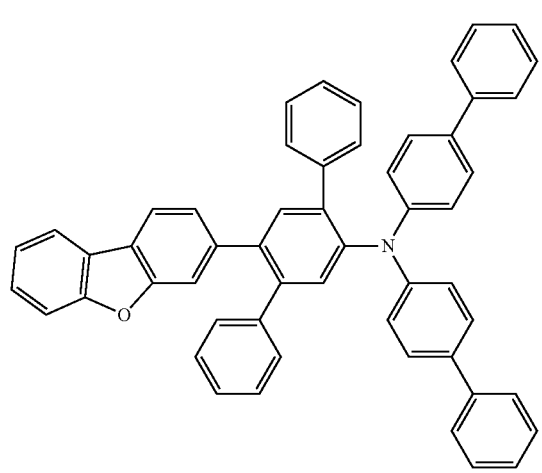
6
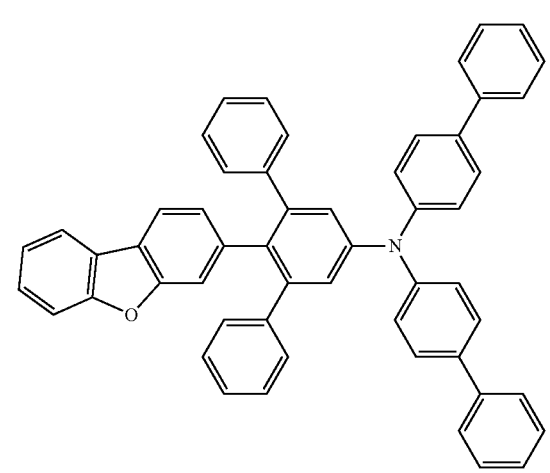
7
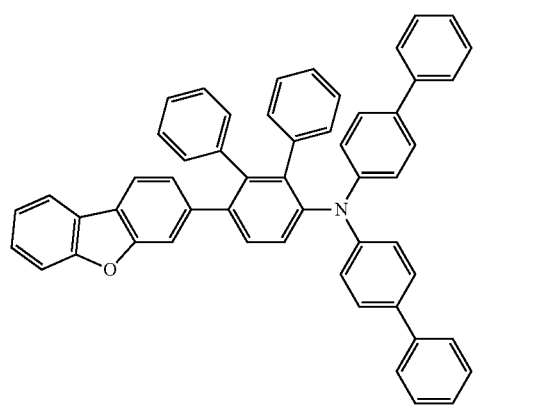
8
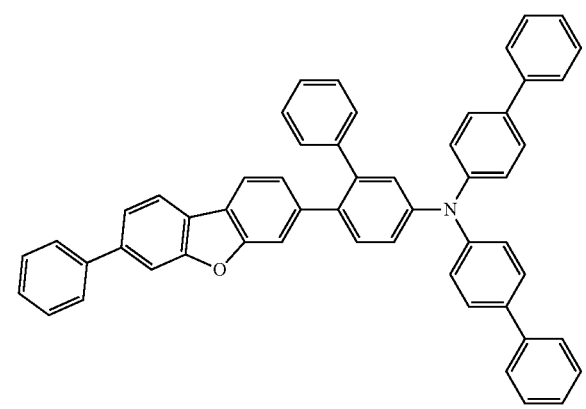
9
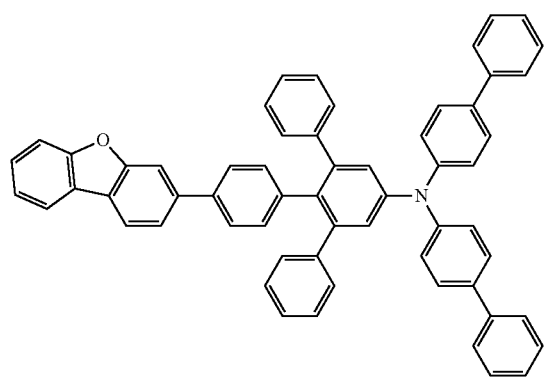
10
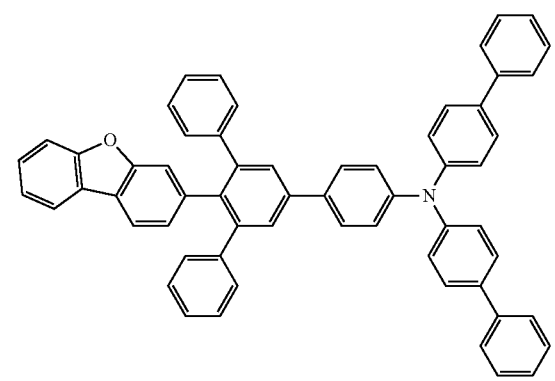

-continued
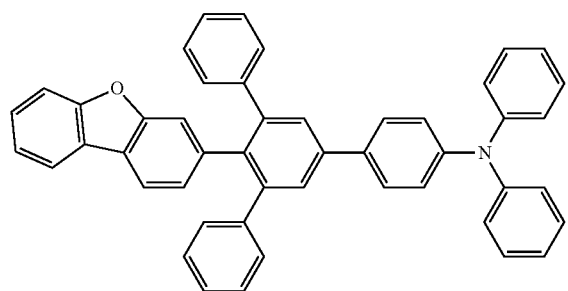
11
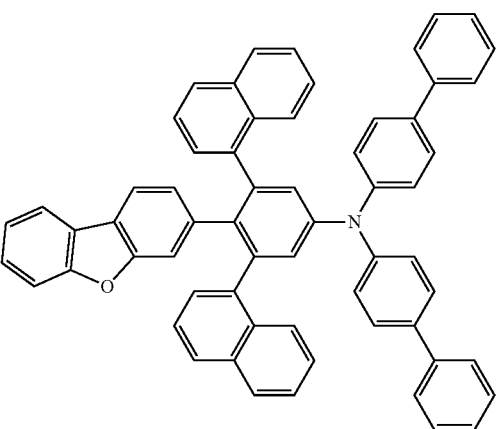
12
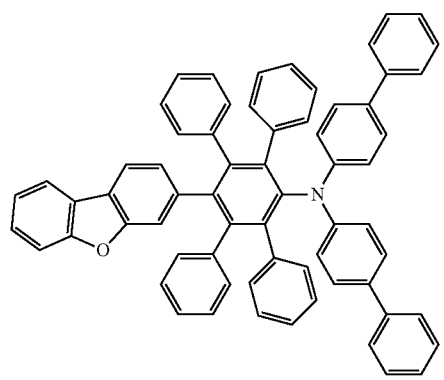
13
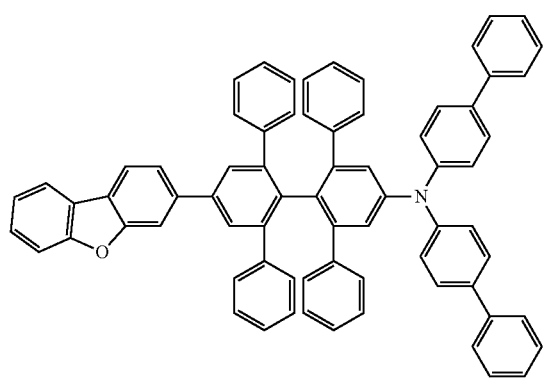
14
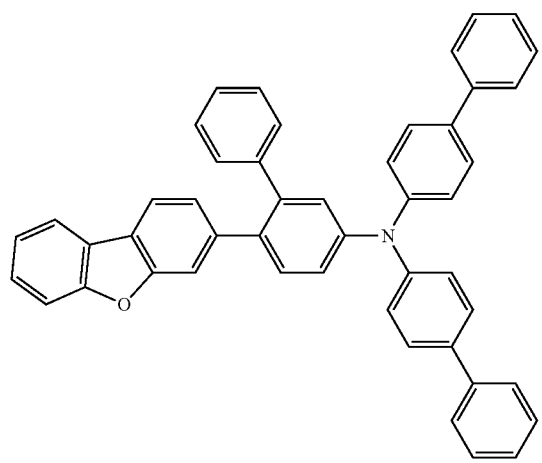
15
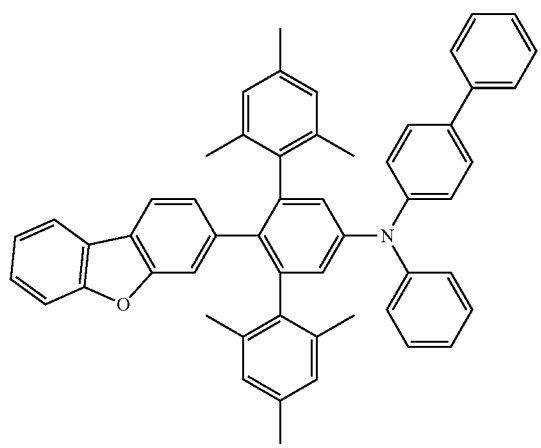
16

-continued
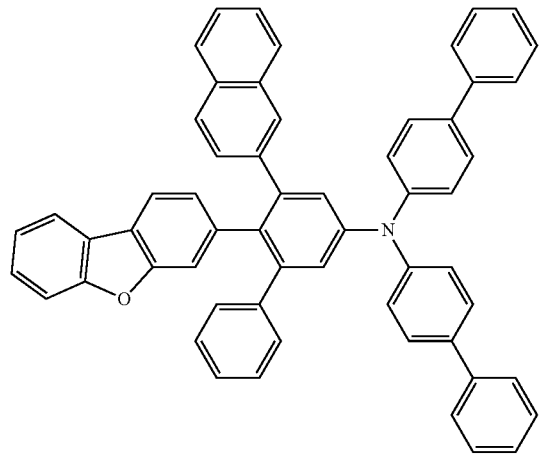
17
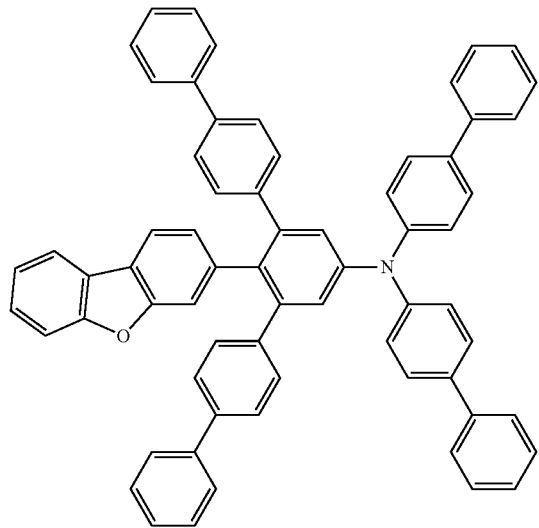
18
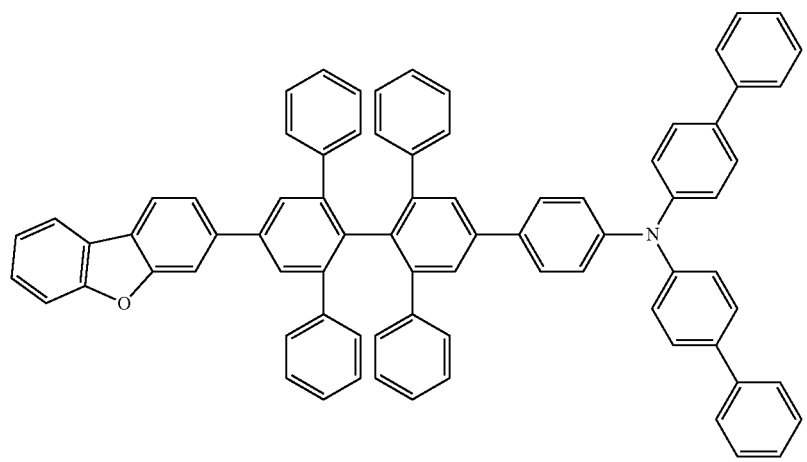
19
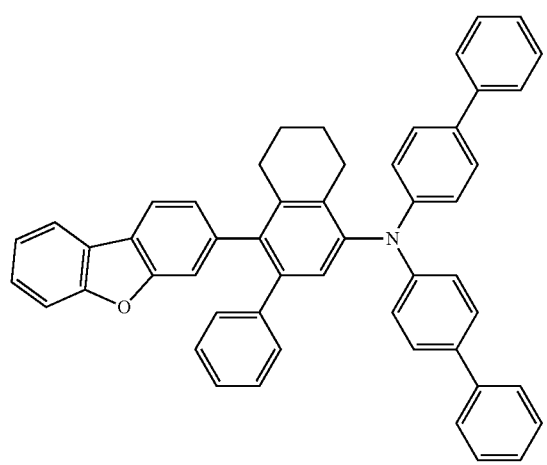
20
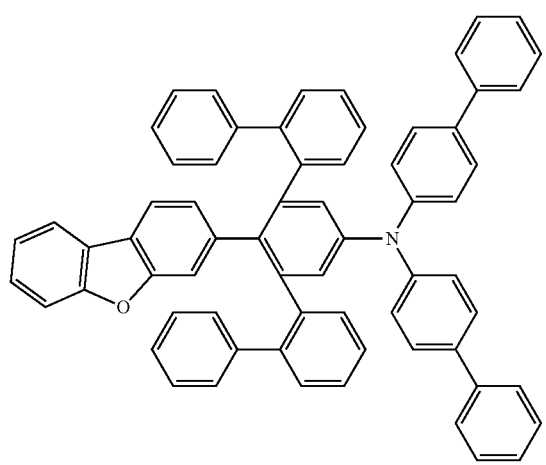
21

-continued
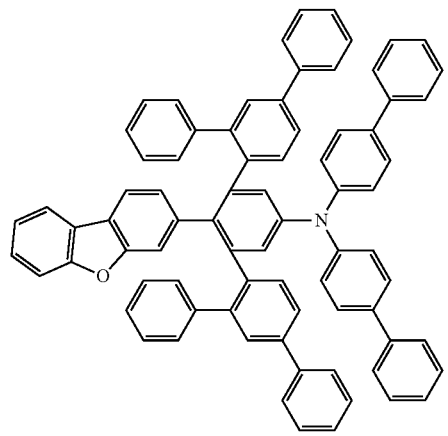
22
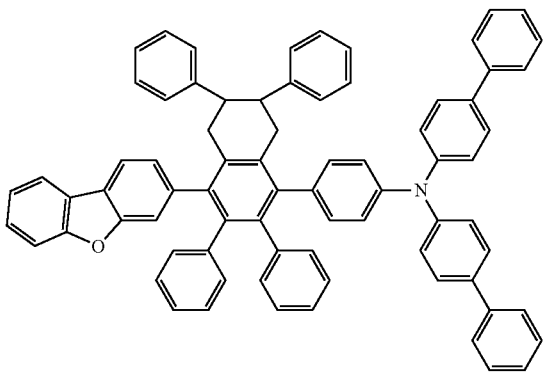
23
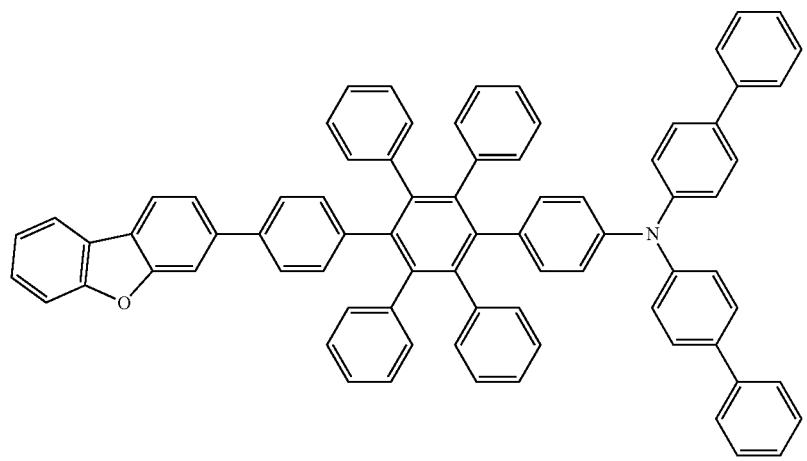
24
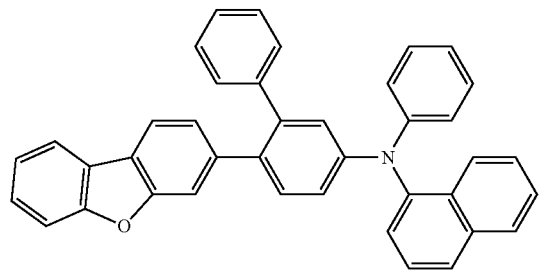
25
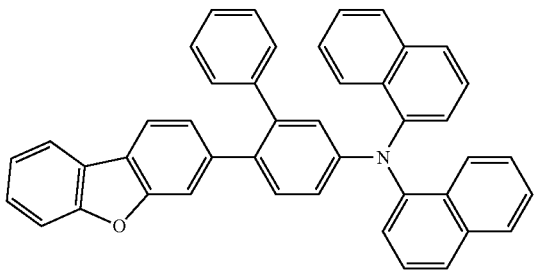
26
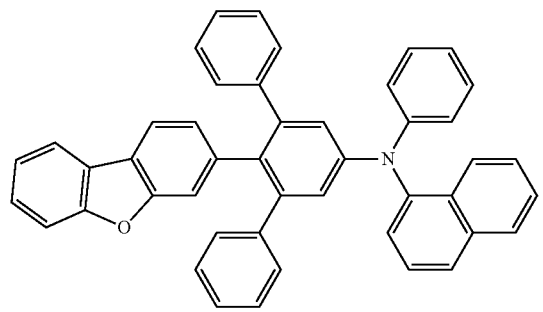
27
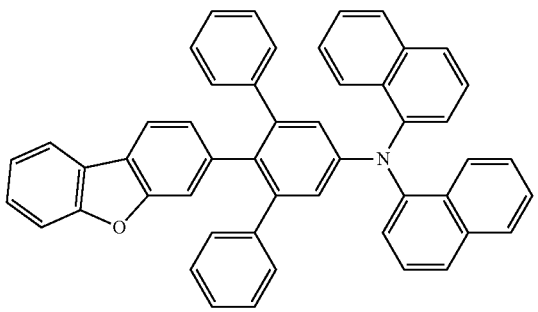
28

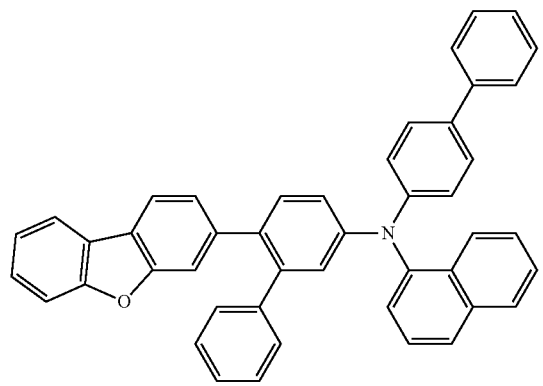
29

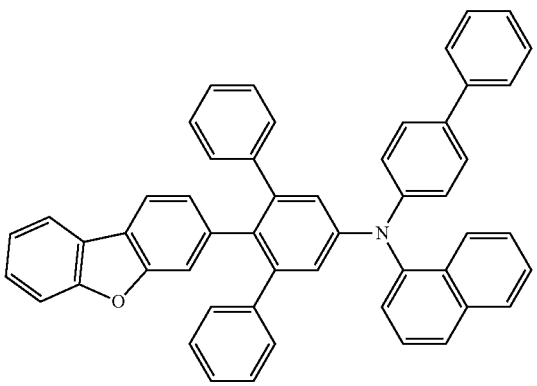
30

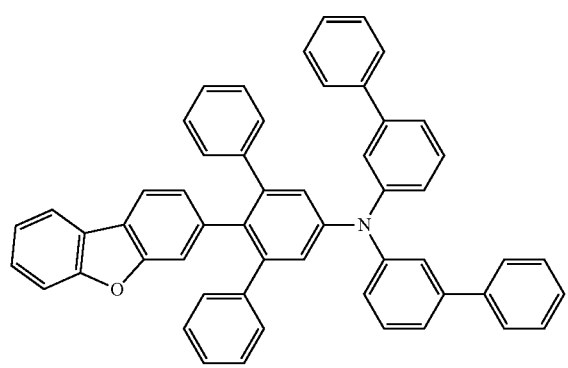
31

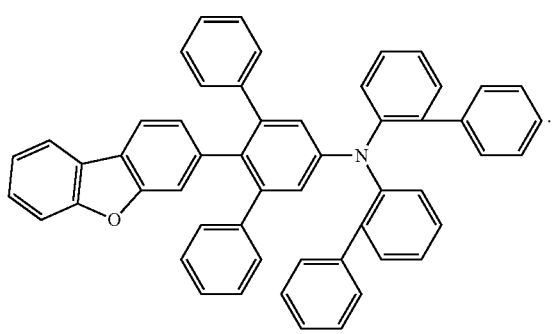
32

7. An organic electroluminescent (EL) device comprising a material for an organic EL device represented by Formula 1 in a layer of stacking layers between an emission layer and an anode:

Formula 1

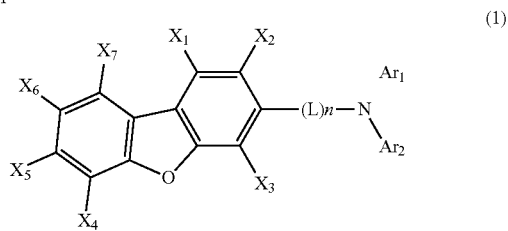
(1)

wherein in Formula 1,
$X_1$ to $X_7$ are each independently hydrogen, deuterium, a halogen atom, an alkyl group having 1 to 15 carbon atoms, or a substituted or unsubstituted aryl group;
$Ar_1$ and $Ar_2$ are each independently a substituted or unsubstituted aryl group having 6 to 12 carbon atoms for forming a ring;
L is a substituted or unsubstituted arylene group;
n is an integer from 1 to 3; and
at least one L is a phenylene group represented by Formula 2:

Formula 2

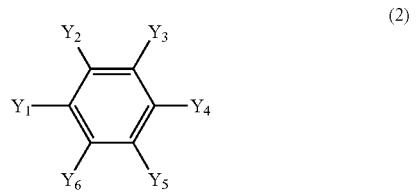
(2)

wherein in Formula 2,
$Y_1$ to $Y_6$ are each independently a direct linkage, hydrogen, deuterium, a halogen atom, an alkyl group having 1 to 15 carbon atoms, an alkenyl group having 2 to 15 carbon atoms, or a substituted or unsubstituted aryl group or may combine with an adjacent group to form a ring;
two of $Y_1$ to $Y_6$ make a direct linkage with a respective adjacent group; and
at least one of $Y_1$ to $Y_6$ of the at least one L is an aryl group;
wherein the material for an organic EL device is comprised in a hole transport layer or a hole injection layer.

8. The organic EL device of claim 7, wherein each of $Y_1$ and $Y_4$ among $Y_1$ to $Y_6$ of the phenylene group represented by Formula 2 makes a direct linkage with a respective adjacent group.

9. The organic EL device of claim 7, wherein at least one of $Y_1$ to $Y_6$ is the aryl group having at least 10 carbon atoms for forming a ring.

10. The organic EL device of claim 7, wherein $Ar_1$ and $Ar_2$ are each independently selected from the group consisting of a phenyl group, a biphenyl group and a naphthyl group.

11. The organic EL device of claim 7, wherein n is 1.

12. The organic EL device of claim 7, wherein the material for an organic EL device is represented by one of Compounds 1 to 32:

51
1
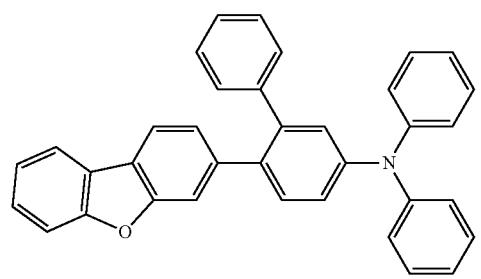
2
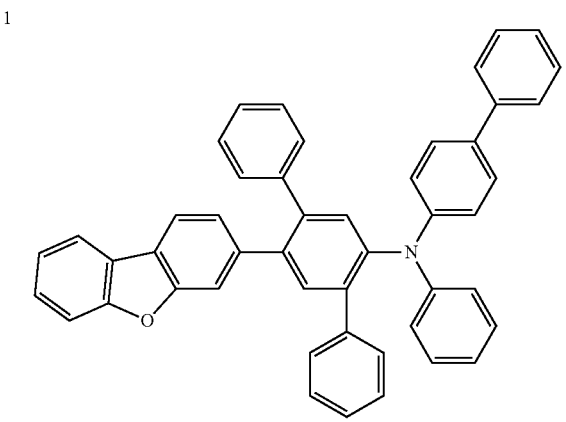
3
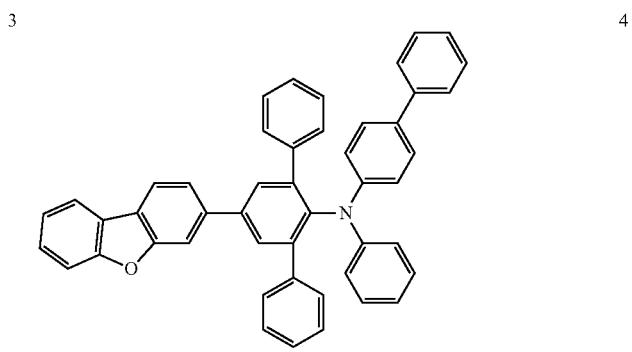
4
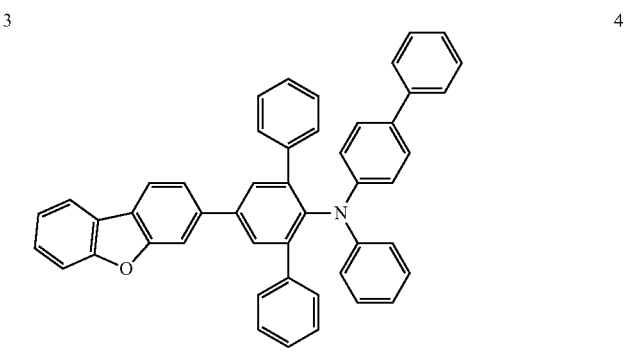
5
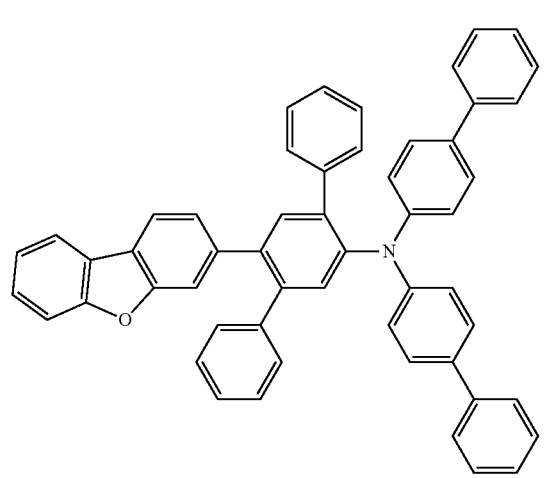
6
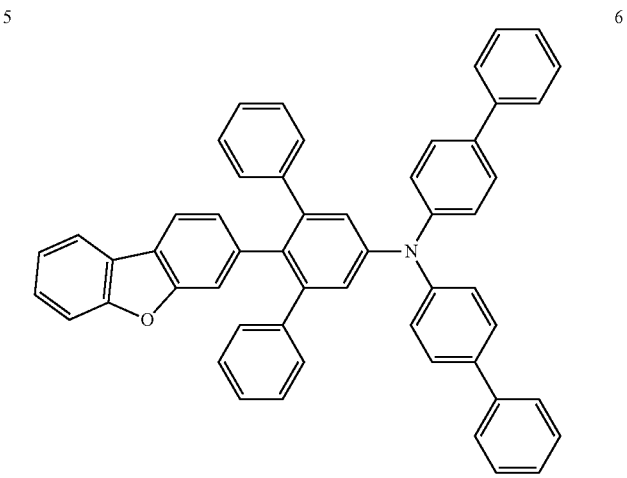
7
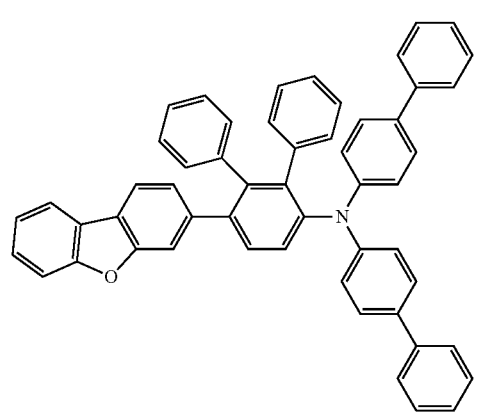
8
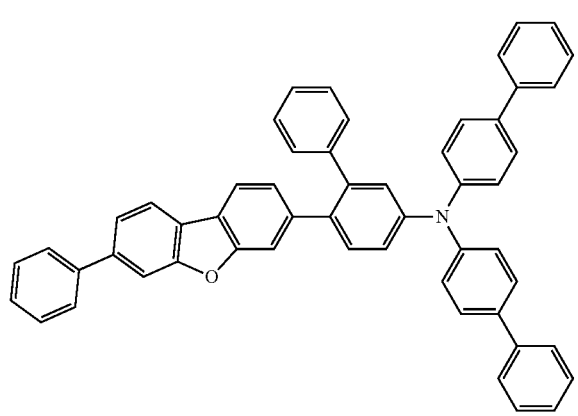

-continued
9
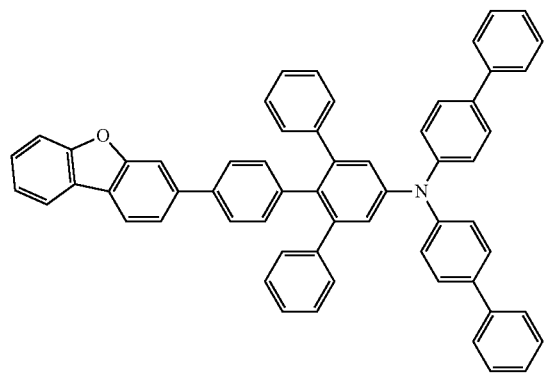
10
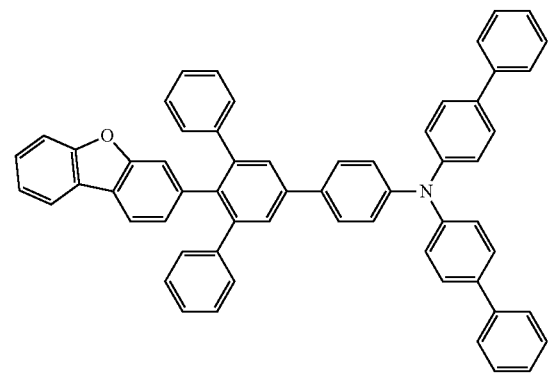
11
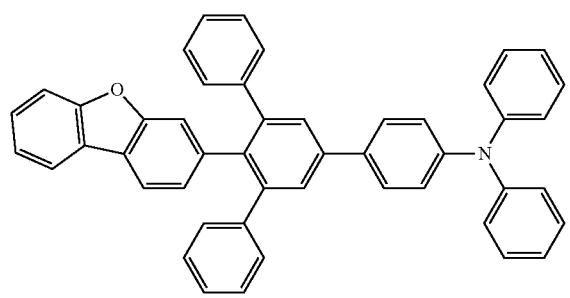
12
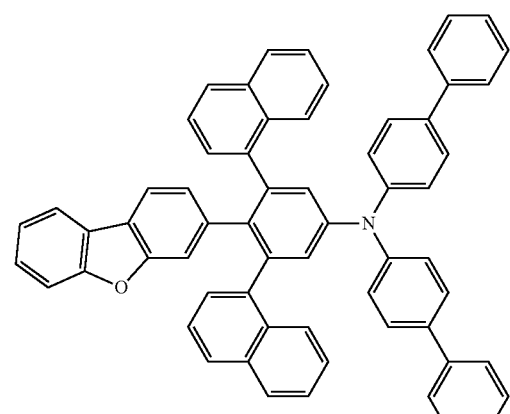
13
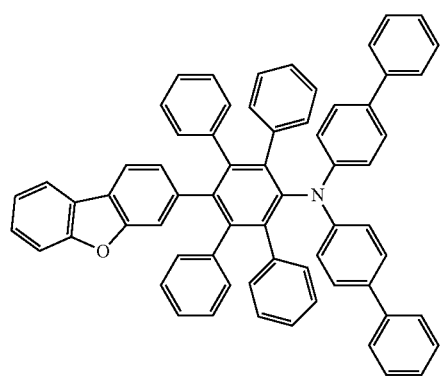
14
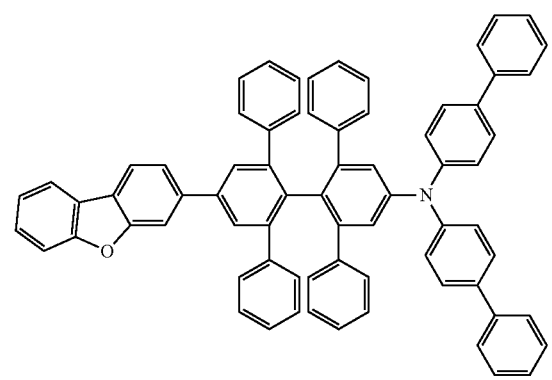
15
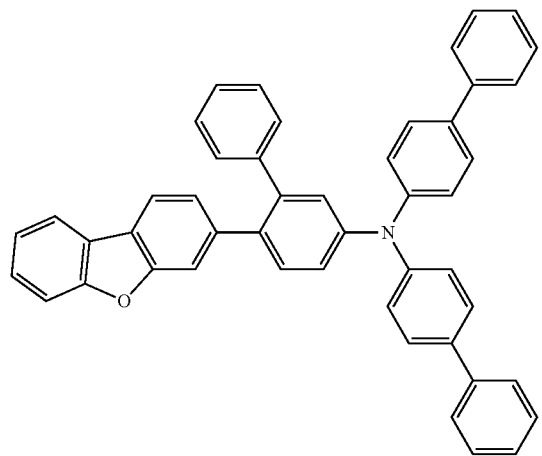
16
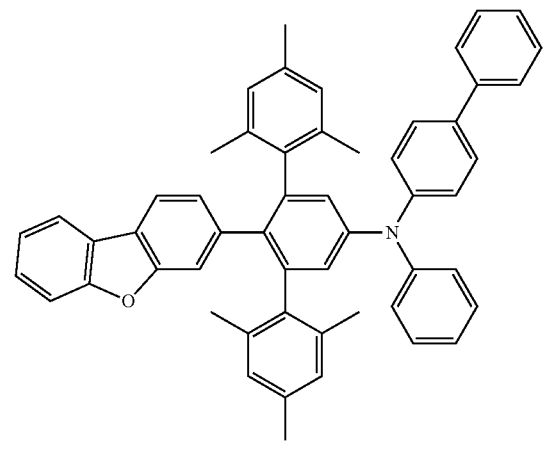

-continued
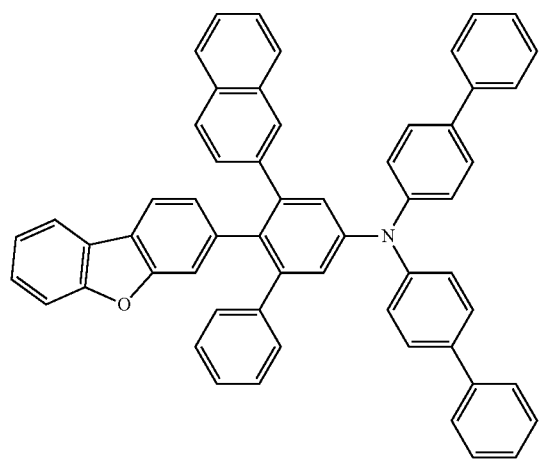
17
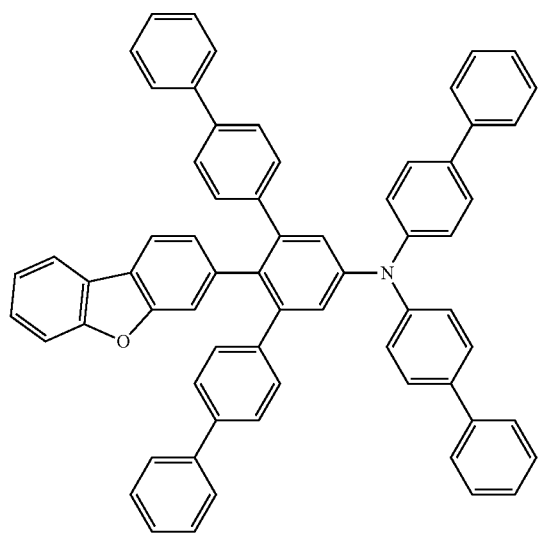
18
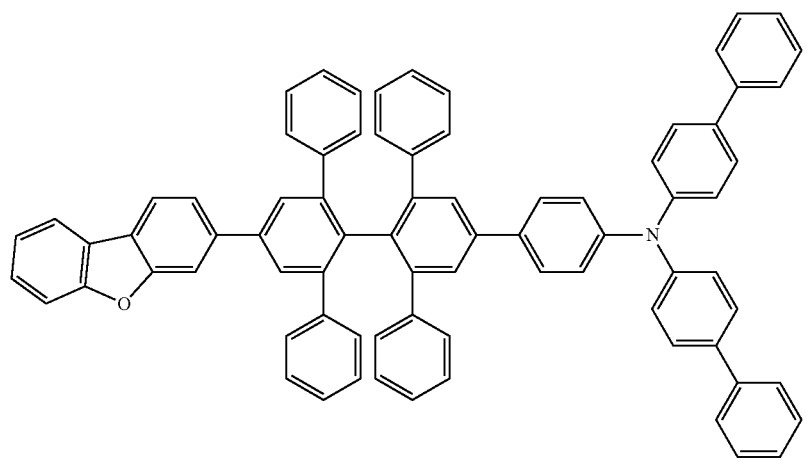
19
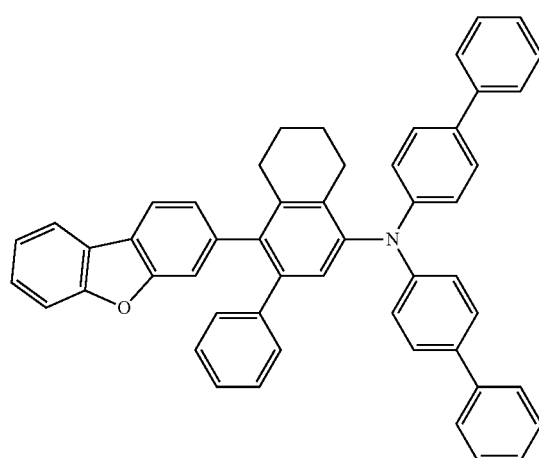
20
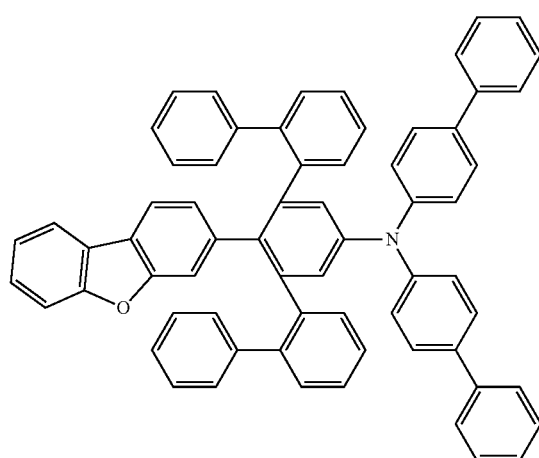
21

-continued
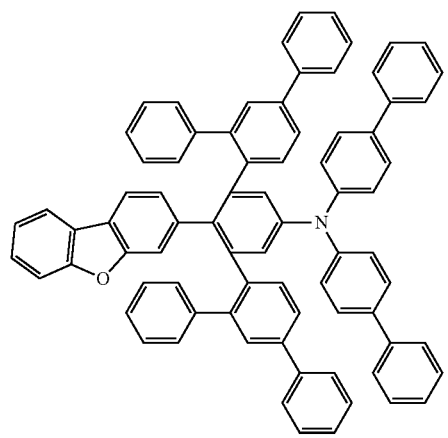
22
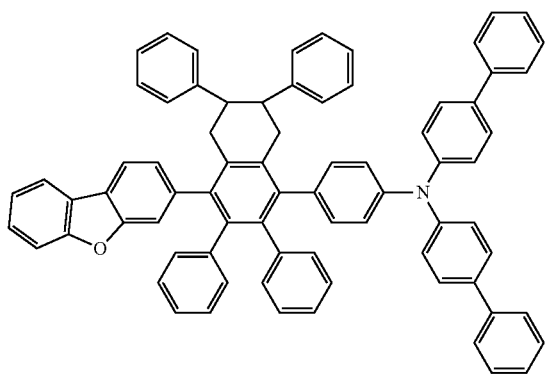
23
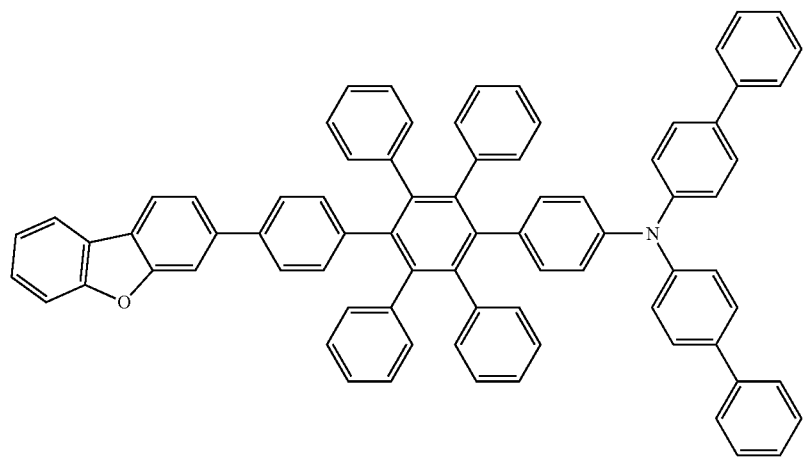
24
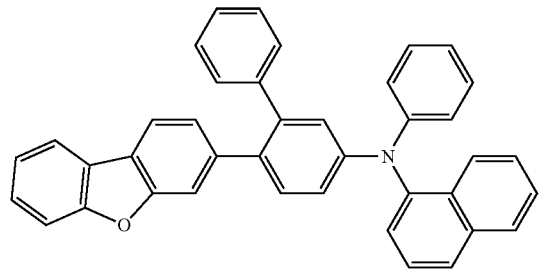
25
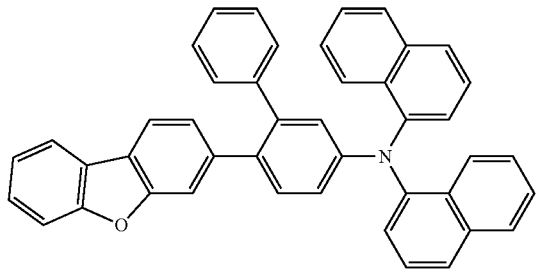
26
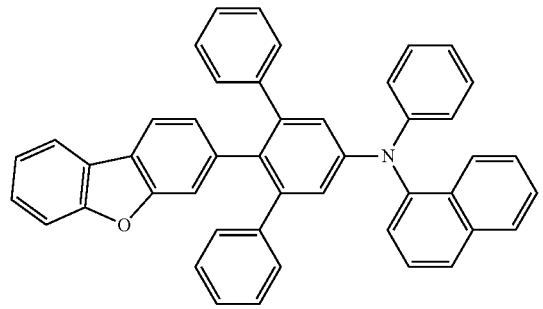
27
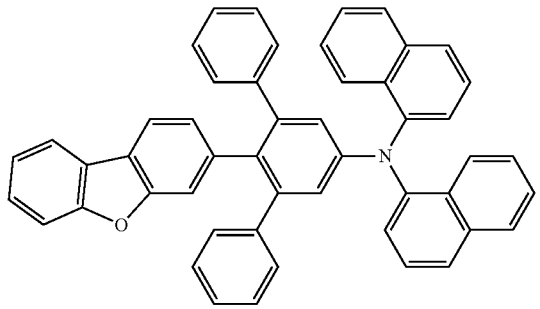
28

-continued
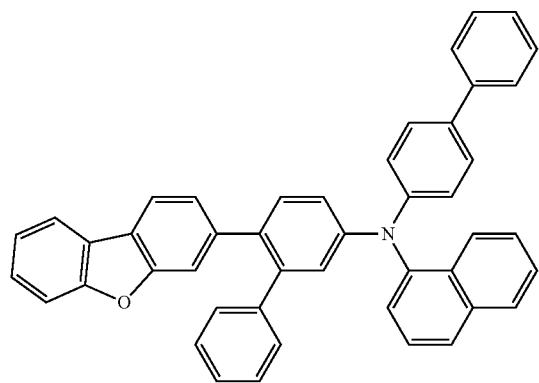
29
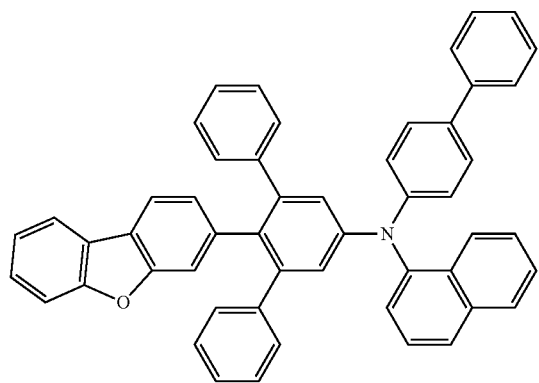
30
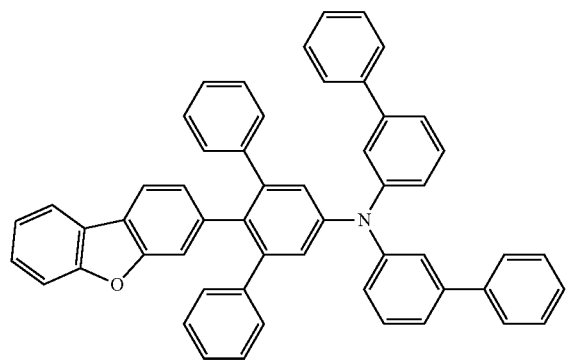
31
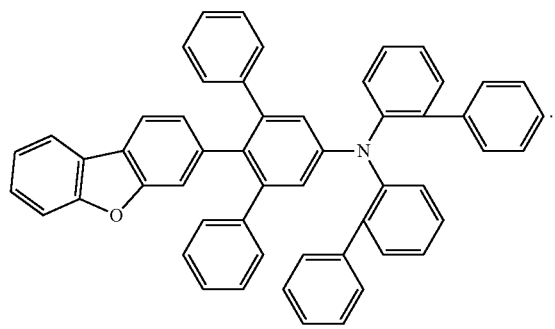
32
* * * * *